US012718934B2

(12) United States Patent
Hastings et al.

(10) Patent No.: US 12,718,934 B2
(45) Date of Patent: Aug. 25, 2026

(54) SYSTEMS AND METHODS FOR MANAGING AIR QUALITY IN A SURGICAL ENVIRONMENT

(71) Applicant: Stryker Corporation, Kalamazoo, MI (US)

(72) Inventors: Sean Victor Hastings, Flower Mound, TX (US); Heather Marlene Coughlan, Brantford (CA)

(73) Assignee: Stryker Corporation, Portage, MI (US)

( * ) Notice: Subject to any disclaimer, the term of this patent is extended or adjusted under 35 U.S.C. 154(b) by 381 days.

(21) Appl. No.: 18/334,339

(22) Filed: Jun. 13, 2023

(65) Prior Publication Data

US 2023/0402165 A1 Dec. 14, 2023

Related U.S. Application Data

(60) Provisional application No. 63/366,397, filed on Jun. 14, 2022.

(51) Int. Cl.
*G16H 40/20* (2018.01)
*F24F 3/167* (2021.01)
(Continued)

(52) U.S. Cl.
CPC ............. *G16H 40/20* (2018.01); *F24F 3/167* (2021.01); *G06V 10/70* (2022.01); *G06V 20/44* (2022.01);
(Continued)

(58) Field of Classification Search
None
See application file for complete search history.

(56) References Cited

U.S. PATENT DOCUMENTS 6,987,448 B2 1/2006 Catton et al.
7,378,975 B1 5/2008 Smith et al.
(Continued)

FOREIGN PATENT DOCUMENTS

CN 202724392 U 2/2013
CN 204618192 U 9/2015
(Continued)

OTHER PUBLICATIONS

Abdelmoghith et al.. "IoT-Based Healthcare Monitoring System: Bedsores Prevention," 2020 Fourth World Conference on Smart Trends in Systems, Security and Sustainability (WorldS4), Jul. 27-28, 2020, London, United Kingdom; pp. 64-69.
(Continued)

*Primary Examiner* — Ariel Mercado-Vargas
(74) *Attorney, Agent, or Firm* — Morrison & Foerster LLP

(57) ABSTRACT

The present disclosure relates generally to improving surgery safety, and more specifically to techniques for managing air quality associated with an operating room. An exemplary method for managing air quality associated with an operating room comprises: detecting a quantity of a substance in the air in the operating room; determining a surgical milestone associated with a surgery in the operating room; identifying a threshold associated with the substance and the surgical milestone of the surgery in the operating room; determining that the quantity of the substance exceeds the threshold associated with the substance and the surgical milestone of the surgery in the operating room; and in accordance with the determination that the quantity of the substance exceeds the threshold associated with the substance and the surgical milestone, outputting a notification that the quantity of the substance exceeds the threshold associated with the substance and the surgical milestone.

20 Claims, 4 Drawing Sheets

100

(51) Int. Cl.

| | |
|---|---|
| ***F24F 11/00*** | (2018.01) |
| ***F24F 110/65*** | (2018.01) |
| ***G06V 10/70*** | (2022.01) |
| ***G06V 20/40*** | (2022.01) |
| ***G16H 20/40*** | (2018.01) |
| *F24F 120/14* | (2018.01) |
| *G16H 40/40* | (2018.01) |

(52) U.S. Cl.
CPC .......... *G16H 20/40* (2018.01); *F24F 2110/65* (2018.01); *F24F 2120/14* (2018.01); *G16H 40/40* (2018.01)

(56) References Cited

U.S. PATENT DOCUMENTS

| | | | |
|---|---|---|---|
| 7,768,414 | B2 | 8/2010 | Abel et al. |
| 8,090,155 | B2 | 1/2012 | Lacey |
| 8,231,664 | B2 | 7/2012 | Kulstad et al. |
| 9,280,884 | B1 | 3/2016 | Schultz et al. |
| 9,442,070 | B1 | 9/2016 | Hug et al. |
| 9,693,891 | B2 | 7/2017 | Macintyre-ellis et al. |
| 9,729,833 | B1 | 8/2017 | Kusens |
| 9,807,475 | B2 | 10/2017 | Subiry |
| 9,934,358 | B2 | 4/2018 | Johnson |
| 9,956,113 | B2 | 5/2018 | Santa Maria et al. |
| 10,020,075 | B2 | 7/2018 | Perlman et al. |
| 10,368,039 | B2 | 7/2019 | Derenne |
| 10,600,204 | B1 | 3/2020 | Rush et al. |
| 10,631,783 | B2 | 4/2020 | Persson |
| 10,688,269 | B2 | 6/2020 | Scharmer et al. |
| 10,729,502 | B1 | 8/2020 | Wolf et al. |
| 10,859,474 | B2 | 12/2020 | Chou et al. |
| 10,904,492 | B2 | 1/2021 | Derenne |
| 10,930,400 | B2 | 2/2021 | Robbins et al. |
| 11,040,155 | B2 | 6/2021 | Hong |
| 11,051,751 | B2 | 7/2021 | Larson et al. |
| 11,076,778 | B1 | 8/2021 | Abbas |
| 11,707,397 | B2 | 7/2023 | Mangiardi |
| 12,207,887 | B1 | 1/2025 | Barral et al. |
| 2002/0174869 | A1* | 11/2002 | Gahan .................. B01D 39/163 128/205.27 |
| 2005/0220662 | A1* | 10/2005 | Hedman ............. A01M 1/2094 422/1 |
| 2006/0084043 | A1 | 4/2006 | Weaver et al. |
| 2006/0234175 | A1 | 10/2006 | Bridgwater et al. |
| 2006/0243720 | A1 | 11/2006 | Koch et al. |
| 2007/0027403 | A1 | 2/2007 | Kosted |
| 2007/0071343 | A1 | 3/2007 | Zipnick et al. |
| 2009/0267776 | A1 | 10/2009 | Glenn et al. |
| 2012/0078144 | A1 | 3/2012 | Sinykin |
| 2012/0268280 | A1 | 10/2012 | Hatch et al. |
| 2014/0039351 | A1 | 2/2014 | Mix et al. |
| 2014/0358044 | A1 | 12/2014 | Kirwan et al. |
| 2015/0310718 | A1 | 10/2015 | Wilson et al. |
| 2016/0061794 | A1 | 3/2016 | Schultz et al. |
| 2016/0061795 | A1 | 3/2016 | Schultz et al. |
| 2016/0120691 | A1 | 5/2016 | Kirwan et al. |
| 2016/0314258 | A1 | 10/2016 | Kusens |
| 2017/0231577 | A1 | 8/2017 | Ben Shalom et al. |
| 2017/0249432 | A1 | 8/2017 | Grantcharov |
| 2017/0281073 | A1 | 10/2017 | Drennan et al. |
| 2017/0296771 | A1* | 10/2017 | Scharmer ........... G01N 27/4141 |
| 2018/0071137 | A1 | 3/2018 | Kuras et al. |
| 2018/0243025 | A1 | 8/2018 | Smits et al. |
| 2018/0247128 | A1 | 8/2018 | Alvi |
| 2018/0289406 | A1* | 10/2018 | Vogt .................. B01F 25/43141 |
| 2019/0104919 | A1 | 4/2019 | Shelton, IV et al. |
| 2019/0104982 | A1 | 4/2019 | Dunn et al. |
| 2019/0201082 | A1* | 7/2019 | Shelton, IV .......... A61M 1/784 |
| 2019/0216516 | A1* | 7/2019 | Vogt ................... A61B 17/8819 |
| 2019/0307405 | A1 | 10/2019 | Terry et al. |
| 2019/0311599 | A1 | 10/2019 | Jensen et al. |
| 2019/0328598 | A1 | 10/2019 | Mangiardi |
| 2019/0371456 | A1 | 12/2019 | Page et al. |
| 2019/0374375 | A1 | 12/2019 | Mcgregor et al. |
| 2019/0374387 | A1 | 12/2019 | Ribble et al. |
| 2020/0113488 | A1 | 4/2020 | Al-ali et al. |
| 2020/0155059 | A1 | 5/2020 | Kayser et al. |
| 2020/0245950 | A1 | 8/2020 | Liang et al. |
| 2020/0246180 | A1 | 8/2020 | Liang et al. |
| 2020/0268457 | A1 | 8/2020 | Wolf et al. |
| 2020/0272660 | A1 | 8/2020 | Wolf |
| 2020/0350063 | A1 | 11/2020 | Thornton |
| 2020/0405217 | A1 | 12/2020 | Jayaraman et al. |
| 2021/0038084 | A1 | 2/2021 | Dion et al. |
| 2021/0125444 | A1 | 4/2021 | Terry |
| 2021/0207840 | A1* | 7/2021 | Clark ....................... F24F 11/64 |
| 2021/0307840 | A1 | 10/2021 | Wolf |
| 2021/0313054 | A1 | 10/2021 | Takahashi et al. |
| 2022/0054687 | A1* | 2/2022 | Forzani ..................... A61L 2/22 |
| 2022/0129822 | A1 | 4/2022 | Donhowe et al. |
| 2022/0296332 | A1 | 9/2022 | Satish et al. |
| 2022/0378520 | A1* | 12/2022 | Shelton, IV ........... G16H 40/63 |
| 2022/0384011 | A1* | 12/2022 | Shelton, IV ......... G05B 19/042 |
| 2022/0399105 | A1 | 12/2022 | Wagner Block et al. |
| 2023/0031655 | A1* | 2/2023 | Hermann ................ F24F 11/32 |
| 2023/0099920 | A1 | 3/2023 | Mao et al. |
| 2023/0210579 | A1 | 7/2023 | Torabi et al. |
| 2023/0317258 | A1 | 10/2023 | Brown |
| 2023/0358629 | A1 | 11/2023 | Kirschman et al. |
| 2023/0402164 | A1 | 12/2023 | Bhardwaj |
| 2023/0402166 | A1 | 12/2023 | Tiwary |
| 2023/0402167 | A1 | 12/2023 | Tiwary |
| 2024/0215800 | A1 | 7/2024 | Shelton, IV et al. |
| 2024/0408370 | A1 | 12/2024 | Saptharishi et al. |

FOREIGN PATENT DOCUMENTS

| | | | |
|---|---|---|---|
| CN | 111352378 | A | 6/2020 |
| CN | 211432863 | U | 9/2020 |
| CN | 112426266 | A | 3/2021 |
| DE | 4339379 | A1 | 5/1995 |
| EP | 2143090 | A1 | 9/2007 |
| EP | 2391317 | A1 | 8/2010 |
| EP | 2619724 | A2 | 7/2013 |
| EP | 3556318 | A1 | 10/2019 |
| WO | 2007/106040 | A1 | 9/2007 |
| WO | 2010/086740 | A1 | 8/2010 |
| WO | 2012/040554 | A2 | 3/2012 |
| WO | 2015/092627 | A1 | 6/2015 |
| WO | 2017/183602 | A1 | 10/2017 |
| WO | 2019/130117 | A1 | 7/2019 |
| WO | 2020/031147 | | 2/2020 |
| WO | 2020/165918 | A1 | 8/2020 |
| WO | 2020/243527 | A1 | 12/2020 |
| WO | 2020/264140 | A1 | 12/2020 |
| WO | 2021/021609 | A1 | 2/2021 |
| WO | 2021/096996 | A1 | 5/2021 |
| WO | 2021/097367 | A1 | 5/2021 |
| WO | 2021/152059 | A1 | 8/2021 |
| WO | 2021/216566 | A1 | 10/2021 |
| WO | 2022/040357 | A1 | 2/2022 |
| WO | 2022/249097 | A2 | 12/2022 |
| WO | 2022/249100 | A1 | 12/2022 |

OTHER PUBLICATIONS

Anderson et al. (Jun. 2014). "Strategies to Prevent Surgical Site Infections in Acute Care Hospitals: 2014 Update," Infection Control and Hospital Epidemiology 35(6): 605-627.

Association of Surgical Technologists. (Apr. 10, 2015). "AST Guidelines for Best Practice in Maintaining Normothermia in the Perioperative Patient," 32 pages.

Barker et al. (1997). "Anaesthetic pollution. Potential sources, their identification and control," Anaesthesia 52:1077-1083.

Berrios-Torres et al., (2017). "Centers for Disease Control and Prevention Guideline for the Prevention of Surgical Site Infection, 2017," JAMA Surgery 152(8): 784-791.

Caron et al. (May 24, 2021) "Emerging Properties in Self-Supervised Vision Transformers," located at https://arxiv.org/abs/2104.14294, (21 pages).

(56) References Cited

OTHER PUBLICATIONS

Chang et al. (1997). "Exposure of Anesthesiologists to Nitrous Oxide during Pediatric Anesthesia," Industrial Health 35 (1):112-118.
Dosovitskiy et al. (Jun. 3, 2021) "An Image is Worth 16x16 Words: Transformers for Image Recognition at Scale," located at https://arxiv.org/abs/2010.11929, (22 pages).
Extended European Search Report dated Nov. 7, 2023, directed to EP Application No. 23178939.7; 8 pages.
Extended European Search Report dated Nov. 7, 2023, directed to EP Application No. 23178978.5; 10 pages.
Extended European Search Report dated Oct. 10, 2023, directed to EP Application No. 23179030.4; 13 pages.
Extended European Search Report dated Oct. 6, 2023, directed to EP Application No. 23179059.3; 14 pages.
Frank et al. (Feb. 1999). "Temperature Monitoring Practices During Regional Anesthesia," International Anesthesia Research Society 88(2): 373-377.
GenTherm. (2021). "Normothermia Astopad™," located at https://gentherm.com/index.php/en/medical/normothermia/astopad; 3 pages.
Gilly et al. (Nov. 1991). "Anesthetic gas contamination in the operating room—an unsolved problem? Results of our own studies," Anaesthesist 40(11):629-637.
Hamilton et al. (Mar. 16, 2022) "Unsupervised Semantic Segmentation by Distilling Feature Correspondences," located at https://arxiv.org/abs/2203.08414, (26 pages).
Hsiao et al. (2016). "Body posture recognition and turning recording system for the care of bed bound patients," Technology and Health Care 24: S307-S312.
Jiang et al. (Aug. 20, 2022) "STC: Spatio-Temporal Contrastive Learning for Video Instance Segmentation," located at https://arxiv.org/abs/2202.03747, (19 pages).
Kanmura et al. (Mar. 1999). "Causes of Nitrous Oxide Contamination in Operating Rooms," Anesthesiology 90 (3):693-696.
Kole. (Oct. 1990). "Environmental and occupational hazards of anesthesia workplace," AANA J 58(5):327-331.
Lam et al. (2022). "Machine learning for technical skill assessment in surgery: a systematic review," Nature Partner Journals 24: 1-16.
Li et al. (Apr. 6, 2021) "Spatial Feature Calibration and Temporal Fusion for Effective One-stage Video Instance Segmentation," located at https://arxiv.org/abs/2104.05606, (10 pages).
Martin. (Dec. 14, 2021). "What Is a Digital Twin?," located at https://blogs.nvidia.com/blog/what-is-a-digital-twin/, (18 pages).
Monroy et al. (Jun. 2020). "Fuzzy monitoring of in-bed postural changes for the prevention of pressure ulcers using inertial sensors attached to clothing," Journal of Biomedical Informatics 107: 1-12.
Nararoff et al. (Apr. 2021). "Tracking Bedridden Patient Positions Using Micro-Doppler Signature," IEEE Sensors Letters 5(4): 1-4.
Omni™. (Nov. 12, 2021) "Omni™ Suite Overview Video," located at https://zimmerbiomet.tv/videos/2521. (9 pages).
Osha. (Jul. 20, 1999). "Anesthetic Gases: Guidelines for Workplace Exposures," located at https://www.osha.gov/waste-anesthetic-gases/workplace-exposures-guidelines, 78 pages.
Pickham et al. (2016). "Evaluating optimal patient-turning procedures for reducing hospital acquired pressure ulcers (LS-HAPU): study protocol for a randomized controlled trial," Trials 17(190.): 1-8.
Sen et al. "Wireless Sensor Patch Suitable for Continuous Monitoring of Contact Pressure in a Clinical Setting," 2018 16th IEEE International New Circuits and Systems Conference (NEWCAS), Jun. 24-27, 2018, Montréal, Canada; pp. 91-95.
Sessler, D. (Aug. 2008). "Temperature Monitoring and Perioperative Thermoregulation," Anesthesiology 109(2): 318-338.
Sigrist, M. (2015). "Mid-infrared laser-spectroscopic sensing of chemical species," Journal of Advanced Research 6: 529-533.
Yengera et al. (May 22, 2018). "Less is More: Surgical Phase Recognition with Less Annotations through Self-SupervisedPre-training of CNN-LSTM Networks," located at https://arxiv.org/abs/1805.08569, (15 pages).
Yojana, A. (2021). "IOT System to Control The Air Quality in Operating Room," Turkish Journal of Computer and Mathematics Education 12(3): 5726-5732.
Özelsel et al. (2018). "Elevated Waste Anaesthetic Gas Concentration in the Paediatric Post-Anaesthesia Care Unit," Turk J Anaesthesiol Reanim 46(5):362-366.
Bhardwaj et al., U.S. Office Action dated Jan. 13, 2025, directed to U.S. Appl. No. 18/334,336; 39 pages.
Tiwary et al., U.S. Office Action dated Feb. 25, 2025, directed to U.S. Appl. No. 18/334,344; 41 pages.
Bhardwaj et al., U.S. Office Action dated Aug. 6, 2025, directed to U.S. Appl. No. 18/334,336; 66 pages.
Intention to Grant dated Jul. 16, 2025, directed to EP Application No. 23 179 030.4; 7 pages.
Office Action dated Sep. 8, 2025, directed to EP Application No. 23 179 059.3; 8 pages.
Tiwary et al., U.S. Office Action dated Jul. 21, 2025, directed to U.S. Appl. No. 18/334,344; 30 pages.
Tiwary et al., U.S. Office Action dated Oct. 28, 2025, directed to U.S. Appl. No. 18/334,344; 24 pages.
Zellmer et al. (2015). "Variation in health care worker removal of personal protective equipment," American Journal of Infection Control 43; pp. 750-751.
Bhardwaj et al., U.S. Office Action dated Dec. 4, 2025, directed to U.S. Appl. No. 18/334,336; 61 pages.
Extended European Search Report dated Dec. 4, 2025, directed to EP Application No. 25216148.4; 9 pages.
Tiwary et al., U.S. Office Action dated Mar. 3, 2026, directed to U.S. Appl. No. 18/334,344; 25 pages.
Tiwary et al., U.S. Office Action dated Mar. 4, 2026, directed to U.S. Appl. No. 18/334,342; 23 pages.

* cited by examiner

SYSTEMS AND METHODS FOR MANAGING AIR QUALITY IN A SURGICAL ENVIRONMENT

CROSS-REFERENCE TO RELATED APPLICATIONS

This application claims the benefit of U.S. Provisional Application No. 63/366,397, filed Jun. 14, 2022, the entire contents of which are hereby incorporated by reference herein.

FIELD

The present disclosure relates generally to improving surgical safety, and more specifically to techniques for managing air quality associated with a surgical environment such as an operating room (OR).

BACKGROUND

Exposure to various substances present in a surgical environment, such as waste anesthetic gases (WAG) and various chemicals, may lead to negative symptoms in patients and healthcare workers, including headaches, fatigue, dizziness, and nausea. Prolonged exposure to these substances may lead to birth defects, cancer, sterility, and liver and kidney diseases. While attempts are made to minimize occupational exposure to WAG through the use of scavenging systems and ventilation systems, these systems may not be properly configured and, furthermore, may malfunction. Further, established best practices may not be diligently observed. Thus, healthcare workers and patients continue to be exposed to potential health risks.

SUMMARY

Disclosed herein are exemplary devices, apparatuses, systems, methods, and non-transitory storage media for managing air quality associated with a surgical environment such as an operating room. An exemplary system can detect a quantity of a substance in the air in the operating room. The substance can be any substance of interest present in the air or the general environment in the operating room. The substance can, for example, comprise an anesthesia gas. Alternatively, or additionally, the substance can, for example, comprise a chemical substance of interest, such as bone cement (e.g., Polymethyl Methacrylate (PMMA), Methyl Methacrylate (MMA)). The system can also determine a surgical milestone associated with a surgery in the operating room. A milestone can refer to a phase or period of time, or a specific time point, during a surgery. Depending on the substance and the surgical milestone, the acceptable range and/or threshold for the substance may differ. The system can determine whether the quantity of the substance exceeds a threshold associated with the substance and the surgical milestone of the surgery in the operating room. If the quantity of the substance exceeds the threshold associated with the substance and the surgical milestone, the system can output a notification that the quantity of the substance exceeds the threshold associated with the substance and the surgical milestone. The alert can prompt a user to check an air management system associated with the operating room, check a WAG scavenging system associated with the operating room, check the waste anesthetic gas disposal (WAGD) system, check for a source of the substance (e.g., check the anesthesia machine to identify possible leaks), review a checklist, or take other appropriate actions to reduce exposure to the substance.

If the quantity of the substance exceeds the threshold associated with the substance and the surgical milestone, the system may additionally or alternatively transmit a control signal to an air management system to adjust the air management system. The air management system can comprise an air ventilation system, such as a positive pressure ventilation system for reducing risks of surgical site infection in the operating room. The control signal can cause an adjustment of the air exchange or turnover rate of the air ventilation system. An increased turnover rate can cause the air to be circulated or recycled at a higher rate to accelerate evacuation of WAG from the surgical environment. The system may additionally or alternatively re-route air flow to a different filtration system. The turnover rate can, for example, be determined by the system based on the substance, a type of the surgery in the operating room, or any combination thereof, as described in detail herein.

If the quantity of the substance exceeds the threshold associated with the substance and the surgical milestone, the system may additionally or alternatively initiate automatic checks to ensure that the air management system is functioning properly. For example, the system can automatically obtain data on the air management system (e.g., a WAG scavenging system) to ensure that it is not disabled or is functioning properly. As another example, the system can automatically obtain data on an anesthesia gas machine to determine whether it is functioning properly. If, for example, the anesthesia gas machine indicates that it is not currently emitting any anesthesia gas, but the threshold for an unacceptable level of anesthesia gas has been triggered, the system may determine that the anesthesia gas machine is leaking. The system can output the results of the automatic checks (e.g., on a dashboard in the OR).

If the quantity of the substance exceeds the threshold associated with the substance and the surgical milestone, the system may additionally, or alternatively, identify a source of the substance (e.g., a leak source) in the operating room. The system can be configured to make the identification using one or more machine-learning models, by receiving one or more images of the operating room captured by one or more cameras and identifying an event (e.g., improper fit of a patient's mask, spill of one or more liquid anesthesia agents) using one or more trained machine-learning models based on the received one or more images. The system can, for example, make the identification using one or more multispectral or hyperspectral imaging sensors.

The system may store the detected quantity of the substance in a database (e.g., a database of the HIS system or EMR system) for various downstream analyses, as described in detail herein. Optionally, the system can determine an update to a surgical protocol by analyzing data in the database. Optionally, the system can recommend, based on historical data and observation of trends, maintenance of equipment (e.g., anesthesia machines, scavenging system, WAG disposal systems, etc.) or facility systems (e.g., HVAC, laminar flow, etc.) through notifications to maintenance teams. For example, if the system determines that a device is not activated to emit a substance (e.g., based on the repository of device state data as described herein), but the substance is nevertheless detected in the environment, the system can recommend that the device be inspected and/or updated by the appropriate maintenance team. As another example, if an unacceptable level of the substance is detected, the system can recommend that the relevant equipment or facility systems be inspected and/or updated within a time frame. As another example, if the system detects an increase of the substance over time, the system can recommend that the relevant equipment or facility systems be inspected and/or updated before the level of the substance reaches an unacceptable level.

Accordingly, examples of the present disclosure may ensure surgical safety and reduce occupational exposure to harmful substances in a surgical environment by monitoring and managing air quality in the environment. The exemplary system can intelligently monitor the presence of target substances in the surgical environment and determine if unsafe thresholds have been triggered based on the type of substance and the status of the surgery. Appropriate measures may be taken automatically by the system during and after the surgery to issue alerts (e.g., within the room and in a centralized command area), improve the air quality of the surgical environment, properly maintain the air management system(s), and improve surgical protocols to reduce health risks from exposure.

An exemplary method for managing air quality associated with an operating room comprises: detecting a quantity of a substance in the air in the operating room; determining a surgical milestone associated with a surgery in the operating room; identifying a threshold associated with the substance and the surgical milestone of the surgery in the operating room; determining that the quantity of the substance exceeds the threshold associated with the substance and the surgical milestone of the surgery in the operating room; and in accordance with the determination that the quantity of the substance exceeds the threshold associated with the substance and the surgical milestone, outputting a notification that the quantity of the substance exceeds the threshold associated with the substance and the surgical milestone.

Optionally, the substance comprises an anesthesia gas.

Optionally, the substance comprises nitrous oxide, desflurane, sevoflurane, enflurane, isoflurane, or any combination thereof.

Optionally, the substance comprises bone cement.

Optionally, the quantity of the substance in the air in the operating room is detected using one or more sensors in the operating room.

Optionally, determining the surgical milestone associated with the surgery comprises: receiving one or more images of the operating room captured by one or more cameras; identifying the surgical milestone from a plurality of predefined surgical milestones using one or more trained machine-learning models based on the received one or more images.

Optionally, the substance comprises an anesthesia gas, and the plurality of predefined surgical milestones comprises: induction, intubation, anesthesia, extubation, or completion of the surgery.

Optionally, the substance comprises bone cement, and the plurality of predefined surgical milestones comprises: a mixing phase, a gun preparation phase, or a gun use phase.

Optionally, the method further comprises: transmitting a control signal to an air management system to adjust the air management system if the quantity of the substance exceeds the threshold associated with the substance and the surgical milestone.

Optionally, the air management system comprises an air ventilation system, and transmitting the control signal to the air management system to adjust the air management system comprises transmitting the control signal to the air ventilation system to adjust a turnover rate of the air ventilation system.

Optionally, the method further comprises: determining the turnover rate based on the substance, a type of the surgery in the operating room, or any combination thereof.

Optionally, the method further comprises: re-routing air flow to a different filtration system if the quantity of the substance exceeds the threshold associated with the substance and the surgical milestone.

Optionally, the method further comprises: identifying a source of the substance in the operating room if the quantity of the substance exceeds the threshold associated with the substance and the surgical milestone.

Optionally, identifying the source of the substance in the operating room comprises: receiving one or more images of the operating room captured by one or more cameras; identifying an event using one or more trained machine-learning models based on the received one or more images.

Optionally, the event is improper fit of a patient's mask, improper insertion of breathing tubes or airway devices, or any combination thereof.

Optionally, the event is spill of one or more liquid anesthesia agents.

Optionally, the source of the substance in the operating room is identified using one or more multispectral or hyperspectral imaging sensors.

Optionally, the notification is an alert to: check an air management system associated with the operating room; check a waste anesthetic gas (WAG) scavenging system associated with the operating room; check the waste anesthetic gas disposal (WAGD) system; check for a source of the substance; review a checklist; or any combination thereof.

Optionally, the checklist is selected based on the substance.

Optionally, the alert is visual, auditory, haptic, or any combination thereof.

Optionally, the alert is displayed on a display in the operating room.

Optionally, the method further comprises: transmitting an alert to a remote anesthesia team or respiratory team if the quantity of the substance exceeds the threshold associated with the substance and the surgical milestone.

Optionally, the method further comprises: transmitting an alert to a maintenance team if the quantity of the substance exceeds the threshold associated with the substance and the surgical milestone.

Optionally, the method further comprises: providing a user interface for specifying the substance for detection.

Optionally, the method further comprises: providing a user interface for specifying the threshold.

Optionally, the method further comprises: storing the detected quantity of the substance in a database.

Optionally, the method further comprises: determining an update to a surgical protocol by analyzing data in the database.

Optionally, the method further comprises: determining if unscheduled or unplanned equipment maintenance is required by analyzing data in the database, wherein the equipment is any one of an air management system, a WAG scavenging system, WAGD system, and an anesthesia machine.

Optionally, determining the surgical milestone associated with a surgery in the operating room comprises: receiving one or more images captured by a camera in the operating room; and providing the one or more images to a machine-learning model.

An exemplary system for managing air quality associated with an operating room comprises: one or more processors;

a memory; and one or more programs, wherein the one or more programs are stored in the memory and configured to be executed by the one or more processors, the one or more programs including instructions for: detecting a quantity of a substance in the air in the operating room; determining a surgical milestone associated with a surgery in the operating room; identifying a threshold associated with the substance and the surgical milestone of the surgery in the operating room; determining that the quantity of the substance exceeds the threshold associated with the substance and the surgical milestone of the surgery in the operating room; and in accordance with the determination that the quantity of the substance exceeds the threshold associated with the substance and the surgical milestone, outputting a notification that the quantity of the substance exceeds the threshold associated with the substance and the surgical milestone.

Optionally, the substance comprises an anesthesia gas.

Optionally, the substance comprises nitrous oxide, desflurane, sevoflurane, enflurane, isoflurane, or any combination thereof.

Optionally, the substance comprises bone cement.

Optionally, the quantity of the substance in the air in the operating room is detected using one or more sensors in the operating room.

Optionally, determining the surgical milestone associated with the surgery comprises: receiving one or more images of the operating room captured by one or more cameras; identifying the surgical milestone from a plurality of predefined surgical milestones using one or more trained machine-learning models based on the received one or more images.

Optionally, the substance comprises an anesthesia gas, and wherein the plurality of predefined surgical milestones comprises: induction, intubation, anesthesia, extubation, or completion of the surgery.

Optionally, the substance comprises bone cement, and wherein the plurality of predefined surgical milestones comprises: a mixing phase, a gun preparation phase, or a gun use phase.

Optionally, the one or more programs further include instructions for: transmitting a control signal to an air management system to adjust the air management system if the quantity of the substance exceeds the threshold associated with the substance and the surgical milestone.

Optionally, the air management system comprises an air ventilation system, and wherein transmitting the control signal to the air management system to adjust the air management system comprises transmitting the control signal to the air ventilation system to adjust a turnover rate of the air ventilation system.

Optionally, the one or more programs further include instructions for: determining the turnover rate based on the substance, a type of the surgery in the operating room, or any combination thereof.

Optionally, the one or more programs further include instructions for re-routing air flow to a different filtration system if the quantity of the substance exceeds the threshold associated with the substance and the surgical milestone.

Optionally, the one or more programs further include instructions for identifying a source of the substance in the operating room if the quantity of the substance exceeds the threshold associated with the substance and the surgical milestone.

Optionally, identifying the source of the substance in the operating room comprises: receiving one or more images of the operating room captured by one or more cameras; identifying an event using one or more trained machine-learning models based on the received one or more images.

Optionally, the event is improper fit of a patient's mask, improper insertion of breathing tubes or airway devices, or any combination thereof.

Optionally, the event is spill of one or more liquid anesthesia agents.

Optionally, the source of the substance in the operating room is identified using one or more multispectral or hyperspectral imaging sensors.

Optionally, the notification is an alert to: check an air management system associated with the operating room; check a waste anesthetic gas (WAG) scavenging system associated with the operating room; check the waste anesthetic gas disposal (WAGD) system; check for a source of the substance; review a checklist; or any combination thereof.

Optionally, the checklist is selected based on the substance.

Optionally, the alert is visual, auditory, haptic, or any combination thereof.

Optionally, the alert is displayed on a display in the operating room.

Optionally, the one or more programs further include instructions for: transmitting an alert to a remote anesthesia team or respiratory team if the quantity of the substance exceeds the threshold associated with the substance and the surgical milestone.

Optionally, the one or more programs further include instructions for: transmitting an alert to a maintenance team if the quantity of the substance exceeds the threshold associated with the substance and the surgical milestone.

Optionally, the one or more programs further include instructions for: providing a user interface for specifying the substance for detection.

Optionally, the one or more programs further include instructions for: providing a user interface for specifying the threshold.

Optionally, the one or more programs further include instructions for: storing the detected quantity of the substance in a database.

Optionally, the one or more programs further include instructions for: determining an update to a surgical protocol by analyzing data in the database.

Optionally, the one or more programs further include instructions for: determining if unscheduled or unplanned equipment maintenance is required by analyzing data in the database, wherein the equipment is any one of an air management system, a WAG scavenging system, WAGD system, and an anesthesia machine.

Optionally, determining the surgical milestone associated with a surgery in the operating room comprises: receiving one or more images captured by a camera in the operating room; and providing the one or more images to a machine-learning model.

An exemplary non-transitory computer-readable storage medium stores one or more programs, the one or more programs comprising instructions, which when executed by one or more processors of an electronic device, cause the electronic device to perform any of the methods described herein.

DETAILED DESCRIPTION

Figure 1:
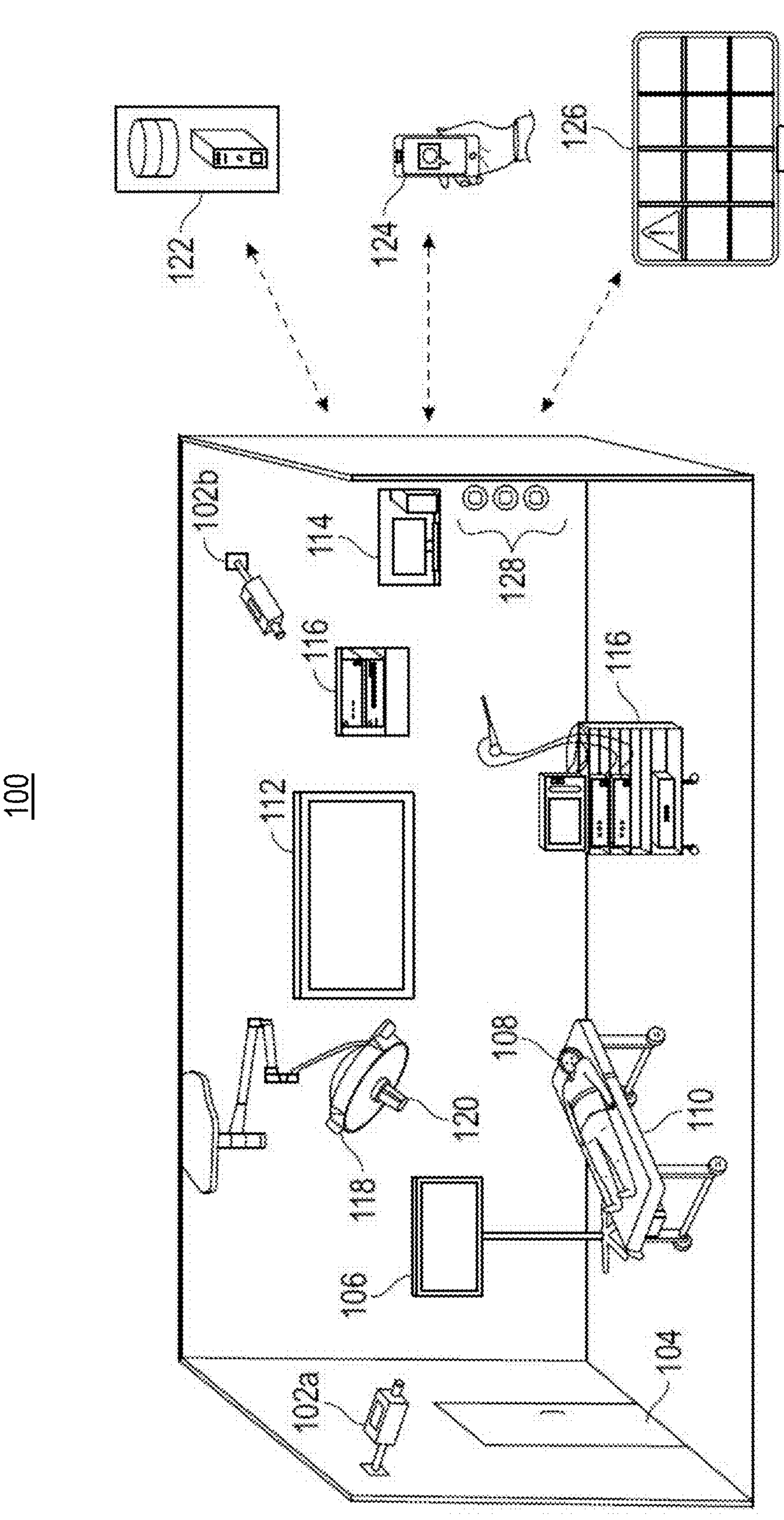
FIG. 1 illustrates an exemplary view of a medical care area.

Disclosed herein are exemplary devices, apparatuses, systems, methods, and non-transitory storage media for managing air quality associated with a surgical environment such as an operating room. An exemplary system can detect a quantity of a substance in the air in the operating room. The substance can be any substance of interest present in the air or the general environment in the operating room. The substance can comprise an anesthesia gas. The substance can comprise a chemical substance of interest, such as bone cement (e.g., Polymethyl Methacrylate (PMMA), Methyl Methacrylate (MMA)). The system can also determine a surgical milestone associated with a surgery in the operating room. A milestone can refer to a phase or period of time during a surgery, or a specific time point during the surgery. Depending on the substance and the surgical milestone, the acceptable range and/or threshold for the substance may differ. The system can determine whether the quantity of the substance exceeds a threshold associated with the substance and the surgical milestone of the surgery in the operating room. If the quantity of the substance exceeds the threshold associated with the substance and the surgical milestone, the system can output a notification that the quantity of the substance exceeds the threshold associated with the substance and the surgical milestone. The alert can prompt a user to check an air management system associated with the operating room, check a WAG scavenging system associated with the operating room, check the WAGD system, check for a source of the substance (e.g., check the anesthesia machine to identify possible leaks), review a checklist, or take other appropriate actions to reduce exposure to the substance.

If the quantity of the substance exceeds the threshold associated with the substance and the surgical milestone, the system may additionally or alternatively transmit a control signal to an air management system to adjust the air management system. The air management system can comprise an air ventilation system, such as a positive pressure ventilation system for reducing risks of surgical site infection in the operating room. The control signal can cause an adjustment of the air exchange or turnover rate of the air ventilation system. An increased turnover rate can cause the air to be circulated or recycled at a higher rate to accelerate evacuation of WAG from the surgical environment. The system may additionally or alternatively re-route air flow to a different filtration system. The turnover rate can, for example, be determined by the system based on the substance, a type of the surgery in the operating room, or any combination thereof, as described in detail herein.

If the quantity of the substance exceeds the threshold associated with the substance and the surgical milestone, the system may additionally or alternatively initiate automatic checks to ensure that the air management system is functioning properly. For example, the system can automatically obtain data on the air management system (e.g., a WAG scavenging system) to ensure that it is not disabled or is functioning properly. As another example, the system can automatically obtain data on an anesthesia gas machine to determine whether it is functioning properly. If, for example, the anesthesia gas machine indicates that it is not currently emitting any anesthesia gas but the threshold for an unacceptable level of anesthesia gas has been triggered, the system may determine that the anesthesia gas machine is leaking. The system can output the results of the automatic checks (e.g., on a dashboard in the OR). The system can e.g. obtain device state data (e.g., whether the anesthesia gas machine is currently running) from the device itself (e.g., via one or more APIs), from a database (e.g., HIS, EMR), from a central controlling device, from one or more user inputs, or any combination thereof. For example, the system can access an electronic repository that stores device state information of a variety of devices in an operating room. The device state data may be normalized based on specific settings of the originating device.

If the quantity of the substance exceeds the threshold associated with the substance and the surgical milestone, the system may additionally or alternatively identify a source of the substance (e.g., a leak source) in the operating room. The system can be configured to make the identification using one or more machine-learning models, by receiving one or more images of the operating room captured by one or more cameras and identifying an event (e.g., improper fit of a patient's mask, spill of one or more liquid anesthesia agents) using one or more trained machine-learning models based on the received one or more images. The system can, for instance, make the identification using one or more multispectral or hyperspectral imaging sensors.

The system may store the detected quantity of the substance in a database (e.g., a database of the HIS system or EMR system) for various downstream analyses, as described in detail herein. The system can be configured to determine an update to a surgical protocol by analyzing data in the database. The system can, for example, recommend, based on historical data and observation of trends, maintenance of equipment (e.g., anesthesia machines, scavenging system, WAG disposal systems, etc.) or facility systems (e.g., HVAC, laminar flow, etc.) through notifications to maintenance teams. For example, if the system determines that a device is not activated to emit a substance (e.g., based on the repository of device state data as described herein), but the substance is nevertheless detected in the environment, the system can recommend that the device be inspected and/or updated by the appropriate maintenance team. As another example, if an unacceptable level of the substance is detected, the system can recommend that the relevant equipment or facility systems be inspected and/or updated within a time frame, such as within one week.

As another example, if the system detects an increase of the substance over time, the system can recommend that the relevant equipment or facility systems be inspected and/or updated before the level of the substance reaches an unacceptable level. The system can, for example, include one or more predictive time-series models. For example, a predictive time-series model can be configured to receive sensor data from one or more previous time points and output a predicted quantity of a substance corresponding to a future time point. The system can then compare the predicted quantity with a threshold (e.g., a predefined threshold associated with the substance and the surgical milestone associated with the future time point) to determine if a follow-up action needs to be taken preemptively. The system can, for instance, be configured to constantly or periodically collect data from various air quality sensors and provide the collected data to the predictive time-series models. This way, the system can generate proper alarms and/or take corrective actions before such substance quantities reach critical predetermined thresholds. For example, the system can activate an HVAC system for a period of time and then automatically shut it off. Continuous monitoring and correcting air quality inside the OR can help to avoid critical situations when air quality quickly deteriorates and it might be too late to take proper actions.

The predictive time-series models can include classical statistical time series analysis (such as AutoRegressive Integrated Moving Average, or ARIMA), shallow machine-learning models (e.g., linear regression, support vector regression), deep machine-learning models, variations of machine-learning models configured to detect and predict anomalies in long-term dependencies, or any combination thereof. Exemplary deep machine-learning models can be found, for example, in Shi et al., "Time Series Forecasting (TSF) Using Various Deep Learning Models," arXiv: 2204.11115v1, available at https://doi.org/10.48550/arXiv.2204.11115. Exemplary anomaly detection and prediction models can be found, for example, in Wei et al., "LSTM-Autoencoder based Anomaly Detection for Indoor Air Quality Time Series Data," arXiv:2204.06701v1, available at https://doi.org/10.48550/arXiv.2204.06701.

Accordingly, examples of the present disclosure may ensure surgical safety and reduce occupational exposure to harmful substances in a surgical environment by monitoring and managing air quality in the environment. The exemplary system can intelligently monitor the presence of target substances in the surgical environment and determine if unsafe thresholds have been triggered based on the type of substance and based on the status of the surgery. Appropriate measures may be taken automatically by the system during and after the surgery to issue alerts (e.g., within the room and in a centralized command area), improve the air quality of the surgical environment, properly maintain the air management system(s), and improve surgical protocols to reduce health risks from exposure.

The following description sets forth exemplary methods, parameters, and the like. It should be recognized, however, that such description is not intended as a limitation on the scope of the present disclosure but is instead provided as a description of exemplary examples.

Although the following description uses terms "first," "second," etc., to describe various elements, these elements should not be limited by these terms. These terms are only used to distinguish one element from another. For example, a first graphical representation could be termed a second graphical representation, and, similarly, a second graphical representation could be termed a first graphical representation, without departing from the scope of the various described examples. The first graphical representation and the second graphical representation are both graphical representations, but they are not the same graphical representation.

The terminology used in the description of the various described examples herein is for the purpose of describing particular examples only and is not intended to be limiting. As used in the description of the various described examples and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an exemplary view of a medical care area 100. In the illustrated example, the medical care area 100 is an operating room where surgical operations are carried out in an antiseptic environment. The medical care area 100 includes one or more doors such as door 104, one or more medical charts, such as chart 106, one or more case carts, a patient, such as patient 108, an operating table, such as operating room table 110, one or more operating room monitors, such as operating room monitor 112, one or more computer systems, such as computer system 114, one or more pieces of medical equipment, such as medical equipment 116, one or more surgical lights, such as surgical light 118, one or more cameras, such as cameras 102*a*, 102*b*, and 120, and/or one or more sensors, such as sensors 128 (e.g., for monitoring various environmental factors). Inside or outside operating room 100, there may be one or more electronic medical record systems (EMR systems), such as electronic medical record system 122, one or more mobile devices, such as mobile device 124, and/or one or more displays, such as display 126. It should be understood that the aforementioned list is exemplary and there may be different, additional or fewer items in or associated with the operating room. For instance, in some examples, the medical care area may include multiple doors, for example, a door that connects to a sterile room where sterile equipment and staff enter/exit through and another door that connects to a non-sterile corridor where patient enters/exits through. Additional exemplary objects that may be found in operating room 100 are provided with reference to FIG. 2.

The cameras (e.g., cameras 102*a*, 102*b*, and 120) can be oriented toward one or more areas or objects of interest in the operating room. For example, one or more cameras can be oriented toward: the door such that they can capture images of the door, the operating table such that they can capture images of the operating table, the patient such that they can capture images of the patient, medical equipment (e.g., X-Ray device, anesthesia machine, staple gun, retractor, clamp, endoscope, electrocautery tool, fluid management system, waste management system, suction units, etc.) such that they can capture images of the medical equipment, surgical staff (e.g., surgeon, anesthesiologist, surgical assistant, scrub nurse, circulating nurse, registered nurse) such that they can capture images of the surgical staff, etc. Multiple cameras can be placed in different locations in the operating room such that they can collectively capture a particular area or object of interest from different perspectives. Some cameras can track a moving object. The one or more cameras can include PTZ cameras. The cameras include cameras that can provide a video stream over a network. The one or more cameras can include a camera integrated into a surgical light in the operating room.

An aspect of the present disclosure is to monitor various target substances (e.g., an anesthesia gas, chemicals of interest) in the air of a surgical environment (e.g., an operating room) and intelligently manage the air quality of the surgical environment. Depending on the status of the surgery in the operating room, the system may operate differently to optimize air management. An exemplary system can detect a quantity of a substance in the air in the operating room and furthermore determine a surgical milestone associated with a surgery in the operating room. A milestone can refer to a phase or period of time during a surgery, or a specific time point during the surgery. Depending on the type of the substance and the surgical milestone, the acceptable range and/or threshold for the substance may differ. The system can determine whether the quantity of the substance exceeds a threshold associated with the substance and the surgical milestone of the surgery in the operating room, and take one or more follow-up actions. The system can output a notification if the quantity of the substance exceeds the threshold associated with the substance and the surgical milestone. The system may additionally or alternatively transmit a control signal to an air management system to adjust the air management system. The system may additionally or alternatively initiate automatic checks to ensure that the air management system is functioning properly. The system may additionally or alternatively identify a source of the substance (e.g., a leak source) in the operating room. The system may store the detected quantity of the substance in a database (e.g., a database of the EMR system) for various downstream analyses. The system can e.g. determine an update to a surgical protocol by analyzing data in the database. The system can e.g. recommend, based on historical data and observation of trends, maintenance of equipment (e.g., anesthesia machines, scavenging system, WAG disposal systems, etc.) or facility systems (e.g., HVAC, laminar flow, etc.) through notifications to maintenance teams. For example, if the system determines that a device is not activated to emit a substance (e.g., based on the repository of device state data as described herein) but the substance is nevertheless detected in the environment, the system can recommend that the device be inspected and/or updated by the appropriate maintenance team. As another example, if an unacceptable level of the substance is detected, the system can recommend that the relevant equipment or facility systems be inspected and/or updated within a time frame. As another example, if the system detects an increase of the substance over time, the system can recommend that the relevant equipment or facility systems be inspected and/or updated before the level of the substance reaches an unacceptable level.

Figure 2:
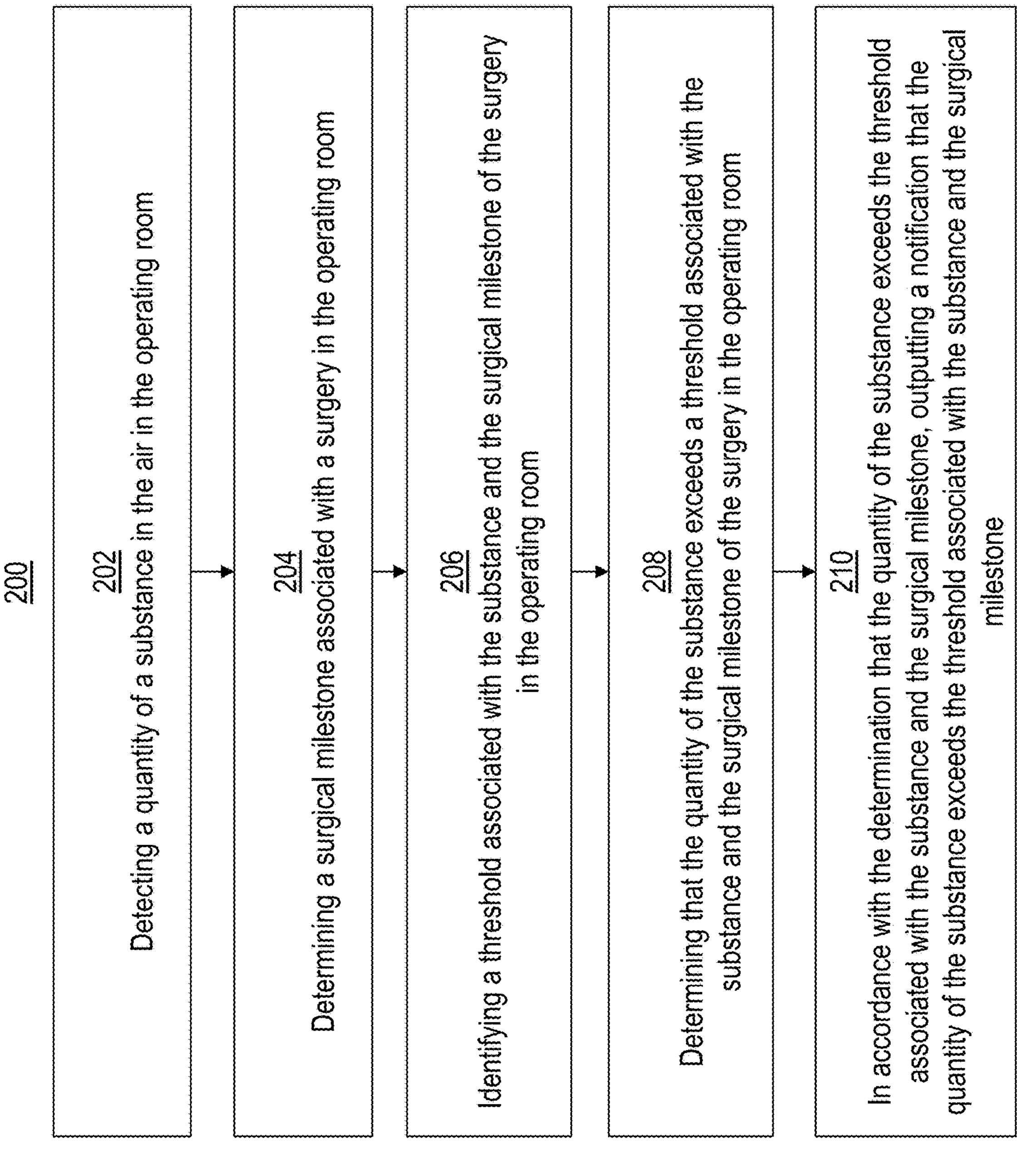
FIG. 2 illustrates an exemplary process for managing air quality associated with an operating room.

FIG. 2 illustrates an exemplary process 200 for managing air quality associated with an operating room. Process 200 is performed, for example, using one or more electronic devices implementing a software platform. In this example, process 200 is performed using a client-server system, and the blocks of process 200 are divided up in any manner between the server and a client device. It will be appreciated that the blocks of process 200 can be divided up between the server and multiple client devices. It will be appreciated that process 200 can be performed using only a client device or only multiple client devices. In process 200, some blocks are, optionally, combined, the order of some blocks is, optionally, changed, and some blocks are, optionally, omitted. Additional steps may be performed in combination with the process 200. Accordingly, the operations as illustrated (and described in greater detail below) are exemplary by nature and, as such, should not be viewed as limiting.

At block 202, an exemplary system (e.g., one or more electronic devices) detects a quantity of a substance in the air in the operating room. The substance can be any substance of interest that may be present in the air or the general environment in the operating room. The substance may comprise an anesthesia gas. The substance may comprise nitrous oxide, vaporized volatile fluorinated liquids (e.g., desflurane, sevoflurane, enflurane, isoflurane desflurane, sevoflurane, enflurane, isoflurane), or any combination thereof. The substance may comprise a chemical substance of interest, such as bone cement (e.g., Polymethyl Methacrylate (PMMA), Methyl Methacrylate (MMA)).

The system may detect and/or measure the substance using one or more sensors in the operating room. As described with reference to FIG. 1, the operating room can include one or more sensors 128 for detecting environmental factors. At least some of the one or more sensors 128 can be configured to detect and/or measure target substances (e.g., gases, chemicals) in the environment. For example, one or more sensors 128 may be located in the operating room to detect any substance of interest that may be present in the air or the general environment in the operating room, such as pellistor/catalytic (CAT) bead sensors, non-dispersive infrared (NDIR) sensors, etc. The system may receive outputs from multiple sensors each configured to detect and/or measure a different type of substance; alternatively, the system may receive outputs from a single sensor configured to detect and/or measure multiple types of substances. For example, an exemplary sensor can utilize photoacoustic engines for multi-gas measurement. The one or more sensors 128 may be placed strategically near devices or locations more susceptible to emitting a substance of interest (e.g., anesthesia machines, area for bone cement mixing).

The system may be configured to detect and/or measure the substance using one or more cameras (e.g., cameras 102*a*, 102*b*, and 120) in the operating room. As described with reference to FIG. 1, the operating room can include one or more cameras (e.g., cameras 102*a*, 102*b*, and 120) oriented toward one or more areas or objects of interest in the operating room. At least some of the cameras can be oriented toward outlets of target substances (e.g., anesthesia mask, cover to the bone cement bowl). The system can analyze the images captured by the cameras (e.g., cameras 102*a*, 102*b*, and 120) to determine whether a leak is depicted or estimate the amount of leakage. The system can, for example, analyze the images using an object-detection/tracking algorithm. The system can, for example, analyze the images using one or more machine-learning models as described herein. The system may issue an alert or notification upon detecting leakage in the images. The cameras may be or may include multispectral/hyperspectral scanners used to detect leaked gases.

At block 204, the system determines a surgical milestone associated with a surgery in the operating room. The system can be configured to determine a plurality of surgical milestones, which are described in detail herein. A milestone may refer to a phase or period of time during a surgical workflow (e.g., surgical phase), or a specific time point during the surgical workflow. A surgical milestone can refer to a preoperative activity, an intraoperative activity, or a postoperative activity, as discussed herein. Some surgical milestones may include specific steps (e.g., making an incision, removing an organ) of a surgery.

The system can be configured to, depending on the type of substance of interest, detect different surgical milestones. For example, if the substance of interest comprises an anesthesia gas, the system may be configured to determine milestones such as the induction phase, the intubation phase, the anesthesia phase, the extubation phase, or completion of the surgery. As another example, if the substance of interest comprises bone cement, the system may be configured to determine milestones such as the mixing phase, the application gun preparation phase, or the application gun use phase.

To determine the surgical milestone associated with the surgery, the system can receive one or more images of the operating room captured by one or more cameras (e.g., cameras 102*a*, 102*b*, 120) and identify the surgical milestone from a plurality of predefined surgical milestones using one or more trained machine-learning models based on the received one or more images.

The one or more images may include video frames. Alternatively, or additionally, the one or more images may include still images. As discussed above, the one or more cameras can be placed inside the operating room. The one or more cameras can be oriented toward: the door such that they can capture images of the door, the operating table such that they can capture images of the operating table, medical equipment (e.g., diagnostic imaging device, anesthesia machine, staple gun, retractor, clamp, endoscope, electrocautery tool) such that they can capture images of the medical equipment, surgical staff (e.g., surgeon, anesthesiologist, surgical assistant, nurse) such that they can capture images of the surgical staff, etc. Multiple cameras can be placed in different locations in the operating room such that they can collectively capture a particular area or object of interest from different perspectives. The one or more cameras can include PTZ cameras. The one or more cameras can include a camera integrated into a surgical light in the operating room.

Multiple cameras may be placed at different angles oriented toward a first door (e.g., a door the patient enters through) and/or a second door (e.g., a door sterile equipment and staff enter through) in the operating room. Multiple cameras may be oriented toward the operating table from different angles. One or more cameras may be oriented toward the surgical lights and the surgeon. Different cameras, depending on the orientation of the camera, may be associated with different models configured to detect different objects such that images captured by a given camera are processed by associated model(s), as described in detail below.

The one or more images can include images captured by one or more surgical devices (e.g., endoscopes). By utilizing images captured by cameras generally installed in the operating room in conjunction with information from surgical devices, the system may provide a more accurate and realistic identification of surgical milestones and estimation of time between surgical milestones (e.g., surgery started, surgery closing).

A surgical milestone can indicate the stage of progression through a surgical procedure or a surgical workflow. The plurality of predefined milestones can include: whether an operating room is ready, whether operating room setup has started, whether a medical staff member (e.g., the surgeon, the scrub nurse, the technician) is donning surgical attire (e.g., masks, gloves, caps, gowns), whether operating room equipment is being set up, whether the patient is brought in to the operating room, whether the patient is ready for intubation or anesthesia, whether a timeout is occurring, whether the timeout has occurred, whether the patient is intubated or anesthetized, whether the patient has been prepped and draped for surgery, whether the patient is ready for surgery, whether a surgery site prep is complete, whether a surgery has started, whether the surgery is closing, whether a dressing is applied to the patient, whether the surgery is stopped, whether the patient is brought out of the operating room, whether the operating room is being cleaned, whether the operating room is clean, or any combination thereof. It should be understood that the foregoing list of milestones is merely exemplary. There may be fewer, additional, or different predefined milestones, for instance, depending on a type of surgical procedure.

The system can be configured to use the one or more trained machine learning models to detect one or more detected objects or events, which are in turn used to determine the one or more surgical milestones (e.g., surgical time points, surgical phases). The one or more trained machine learning models can include an object detection algorithm, an object tracking algorithm, a video action detection algorithm, an anomaly detection algorithm, or any combination thereof.

The system can first use an object detection algorithm to detect a particular type of object in an image, and then use an object tracking algorithm to track the movement and/or status of the detected object in subsequent images. Using one or more object detection algorithms, the system may detect one or more objects and assign an object ID to each detected object. The one or more object detection algorithms can comprise machine-learning models such as a 2D convolutional neural network (CNN) or 3D-CNN (e.g., MobileNetV2, ResNet, MobileNetV3, CustomCNN). After the objects are detected, the system may then use one or more object tracking algorithms to track the movement of the detected objects. The one or more object tracking algorithms can comprise any computer-vision algorithms for tracking objects and can comprise non-machine-learning algorithms. The object tracking algorithm(s) may involve execution of more lightweight code than the object detection algorithm (s), thus improving efficiency and reducing latency for surgical milestone determination. An object detection algorithm can include an instance segmentation algorithm, which can be configured to simultaneously perform classification (e.g., determining what type of object an image depicts), semantic segmentation (e.g., determining what pixels in the image belong to the object), and instance association (e.g., identifying individual instances of the same class; for example, person1 and person2). Additionally, in real-world scenes, a given visual object may be occluded by other objects. Although human vision systems can locate and recognize severely occluded objects with temporal context reasoning and prior knowledge, it may be challenging for classical video understanding systems to perceive objects in the heavily occluded video scenes. Accordingly, some examples of the present disclosure include machine-learning algorithms that take into account the temporal component of the video stream. For example, the system may perform spatial feature calibration and temporal fusion for effective one-stage video instance segmentation. As another example, the system may perform spatio-temporal contrastive learning for video instance segmentation. Additional information on these exemplary algorithms can be found, for example, in Li et al., "Spatial Feature Calibration and Temporal Fusion for Effective One-stage Video Instance Segmentation", arXiv:2104.05606v1, available at https://doi.org/10.48550/arXiv.2104.05606, and Jiang et al., "STC: Spatio-Temporal Contrastive Learning for Video Instance Segmentation", arXiv:2202.03747v1, available at https://doi.org/10.48550/arXiv.2202.03747, both of which are incorporated herein by reference.

The tracked movement and/or status of one or more detected objects can then be used to determine events occurring in the operating room. For example, the system can first use an object detection model to detect a stretcher in an image and then use an object tracking algorithm to detect when the stretcher crosses door coordinates to determine that the stretcher is being moved into the operating room (i.e., an event). The one or more trained machine-learning models can be trained using a plurality of annotated images (e.g., annotated with labels of object(s) and/or event (s)). Further description of such machine learning models is provided below with reference to FIG. 3A.

An object that the system can detect can include physical items, persons, or parts thereof, located inside, entering, or leaving an operating room. The object can e.g. include a stretcher, a patient, a surgeon, an anesthesiologist, the surgeon's hand, a surgical assistant, a scrub nurse, a technician, a nurse, a scalpel, sutures, a staple gun, a door to a sterile room, a door to a non-sterile corridor, a retractor, a clamp, an endoscope, an electrocautery tool, an intubation mask, a surgical mask, a C-Arm, an Endoscopic Equipment Stack, an anesthesia machine, an anesthesia cart, a fluid management system, a waste management system, a waste disposal receptacle, an operating table, surgical table accessories, an equipment boom, an anesthesia boom, an endoscopic equipment cart, surgical lights, a case cart, a sterile back table, a sterile mayo stand, a cleaning cart, an X-Ray device, an imaging device, a trocar, a surgical drape, operating room floor, EKG leads, ECG leads, bed linens, a blanket, a heating blanket, a lap belt, safety straps, a pulse oximeter, a blood pressure machine, an oxygen mask, an IV, or any combination thereof.

An event that the system can detect can include a status, change of status, and/or an action associated with an object. The event can e.g. include whether the surgical lights are turned off, whether the operating table is vacant, whether the bed linens are wrinkled, whether the bed linens are stained, whether the operating table is wiped down, whether a new linen is applied to the operating table, whether a first sterile case cart is brought into the operating room, whether a new patient chart is created, whether instrument packs are distributed throughout the operating room, whether booms and suspended equipment are repositioned, whether the operating table is repositioned, whether a nurse physically exposes instrumentation by unfolding linen or paper, or opening instrumentation containers using a sterile technique, whether the scrub nurse entered the operating room, whether the technician entered the operating room, whether the scrub nurse is donning a gown, whether the circulating nurse is securing the scrub nurse's gown, whether the scrub nurse is donning gloves using the sterile technique, whether the sterile back table or the sterile mayo stand is being set with sterile instruments, whether the patient is wheeled into the operating room on a stretcher, whether the patient is wheeled into the operating room on a wheel chair, whether the patient walked into the operating room, whether the patient is carried into the operating room, whether the patient is transferred to the operating table, whether the patient is covered with the blanket, whether the lap belt is applied to the patient, whether the pulse oximeter is placed on the patient, whether the EKG leads are applied to the patient, whether the ECG leads are applied to the patient, whether the blood pressure cuff is applied to the patient, whether a surgical sponge and instrument count is conducted, whether a nurse announces a timeout, whether a surgeon announces a timeout, whether an anesthesiologist announces a timeout, whether activities are stopped for a timeout, whether the anesthesiologist gives the patient the oxygen mask, whether the patient is sitting and leaning over with the patient's back cleaned and draped, whether the anesthesiologist inspects the patient's anatomy with a long needle, whether the anesthesiologist injects medication into the patient's back, whether the anesthesiologist indicates that the patient is ready for surgery, whether the patient is positioned for a specific surgery, whether required surgical accessories are placed on a table, whether padding is applied to the patient, whether the heating blanket is applied to the patient, whether the safety straps are applied to the patient, whether a surgical site on the patient is exposed, whether the surgical lights are turned on, whether the surgical lights are positioned to illuminate the surgical site, whether the scrub nurse is gowning the surgeon, whether the scrub nurse is gloving the surgeon, whether skin antiseptic is applied, whether the surgical site is draped, whether sterile handles are applied to the surgical lights, whether a sterile team member is handing off tubing to a non-sterile team member, whether a sterile team member is handing off electrocautery to a non-sterile team member, whether the scalpel is handed to the surgeon, whether an incision is made, whether the sutures are handed to the surgeon, whether the staple gun is handed to the surgeon, whether the scrub nurse is handing a sponge to a sponge collection basin, whether an incision is closed, whether dressing is applied to cover a closed incision, whether the surgical lights are turned off, whether the anesthesiologist is waking the patient, whether the patient is returned to a supine position, whether extubation is occurring, whether instruments are being placed on the case cart, whether a garbage bag is being tied up, whether the bed linens are collected and tied up, whether the operating table surface is cleaned, whether the operating room floor is being mopped, whether the patient is being transferred to a stretcher, whether the patient is being brought out of the operating room, whether the surgical table is dressed with a clean linen, whether a second sterile case cart is brought into the operating room, or any combination thereof.

Instead of using trained machine-learning models to detect objects/events (which are then used to determine surgical milestones), the system can use trained machine-learning models to output surgical milestones directly. A trained machine-learning model of the one or more trained machine-learning models can be a machine-learning model (e.g., deep-learning model) trained using annotated surgical video information, where the annotated surgical video information includes annotations of at least one of the plurality of predefined surgical milestones. Further description of such machine learning models is provided below with reference to FIG. 3B.

The system may perform a spatial analysis (e.g., based on object detection/tracking as discussed above), a temporal analysis, or a combination thereof. The system may perform the temporal analysis using a temporal deep neural network (DNN), such as LSTM, Bi-LSTM, MS-TCN, etc. The DNN may be trained using one or more training videos in which the start time and the end time of various surgical milestones are bookmarked. The temporal analysis may be used to predict remaining surgery duration, as discussed below.

The one or more trained machine-learning models used herein can comprise a trained neural network model, such as a 2D CNN, 3D-CNN, temporal DNN, etc. For example, the models may comprise ResNet50, AlexNet, Yolo, I3D ResNet 50, LSTM, MSTCN, etc. The one or more trained machine-learning models may comprise supervised learning models that are trained using annotated images such as human-annotated images. Additionally or alternatively, the one or more trained machine-learning model may comprise self-supervised learning models where a specially trained network can predict the remaining surgery duration, without relying on labeled images. As examples, a number of exemplary models are described in G. Yengera et al., "Less is More: Surgical Phase Recognition with Less Annotations through Self-Supervised Pre-training of CNN-LSTM Networks," arXiv:1805.08569 [cs.CV], available at https://arxiv.org/abs/1805.08569. For example, an exemplary model may utilize a self-supervised pre-training approach based on the prediction of remaining surgery duration (RSD) from laparoscopic videos. The RSD prediction task is used to pre-train a CNN and long short-term memory (LSTM) network in an end-to-end manner. The model may utilize all available data and reduces the reliance on annotated data, thereby facilitating the scaling up of surgical phase recognition algorithms to different kinds of surgeries. Another example model may comprise an end-to-end trained CNN-LSTM model for surgical phase recognition. It should be appreciated by one of ordinary skill in the art that other types of object detection algorithms, object tracking algorithms, video action detection algorithms, that provide sufficient performance and accuracy (e.g., in real time) can be used. The system can include machine-learning models associated with a family of architectures based on visual transformers, which may perform image recognition at scale. An exemplary framework is a Self-supervised Transformer with Energy-based Graph Optimization (STEGO) and may be capable of jointly discovering and segmenting objects without any human supervision. Building upon another self-supervised architecture, DINO, STEGO can distill pre-trained unsupervised visual features into semantic clusters using a novel contrastive loss. Additional information on visual transformers can be found, for example, in Caron et al., "An Image is Worth 16×16 Words: Transformers for Image Recognition at Scale", arXiv:2010.11929v2, available at https://doi.org/10.48550/arXiv.2010.11929, which is incorporated herein by reference. Additional information on DINO and STEGO can be found, for example, in Hamilton et al., "Unsupervised Semantic Segmentation by Distilling Feature Correspondences", arXiv:2203.08414v1, available at https://doi.org/10.48550/arXiv.2203.08414, and Caron et al., "Emerging Properties in Self-Supervised Vision Transformers", arXiv:2104.14294v2, available at https://doi.org/10.48550/arXiv.2104.14294, which are incorporated herein by reference. Additional details related to detection of surgical milestones can be found in U.S. Provisional Application No. 63,366,398 entitled "SYSTEMS AND METHODS FOR MONITORING SURGICAL WORKFLOW AND PROGRESS", which is incorporated herein by reference.

At block 206, the system identifies a threshold associated with the substance and the surgical milestone of the surgery in the operating room. The system can access a threshold database/repository storing a plurality of thresholds, each threshold specific to a given milestone and a given substance. Based on the detected substance in block 202 and the determined surgical milestone in block 205, the system can retrieve the corresponding threshold associated with the substance and the surgical milestone.

Depending on the type of substance and the surgical milestone, the acceptable range and/or threshold for the substance may differ. As an example, if the substance comprises an anesthesia gas, the system may use a first threshold for detecting an unacceptable level of the anesthesia gas during the induction phase, a second threshold for detecting an unacceptable level of the anesthesia gas during the intubation phase, a third threshold for detecting an unacceptable level of the anesthesia gas during the during-operation/anesthesia phase, a fourth threshold for detecting an unacceptable level of the anesthesia gas during the extubation phase, and a fifth threshold for detecting an unacceptable level of the anesthesia gas between cases or surgeries. The first threshold, the second threshold, and/or the fourth threshold may be higher than the third threshold and/or the fifth threshold. This may be because higher levels of anesthesia gas may be expected in the environment during the induction phase, the intubation phase, and/or the extubation phase; accordingly, the associated thresholds may be relatively higher to prevent excessive triggering of the thresholds. On the other hand, lower levels of anesthesia gas may be expected during the actual operation and between cases (unless there is leakage); accordingly, the associated thresholds may be relatively lower such that any unexpected leakage may be detected. The thresholds can be stored in a threshold database/repository as described herein. Accordingly, based on the detected substance in block 202 (e.g., anesthesia gas) and the determined surgical milestone in block 204, the system can retrieve the corresponding threshold associated with anesthesia gas and the detected surgical milestone.

Optionally, there are no thresholds associated with a certain phase of the surgery because there is a low risk of leakage or exposure during that phase. For example, the system can forego determining whether the quantity of the anesthesia gas exceeds a threshold during the setup phase because the anesthesia gas machine has not been turned on. In some examples, during the low-risk phases, the system can forego receiving outputs from the sensors or turn off the sensors altogether.

As another example, if the substance comprises bone cement, the system may use a first threshold for detecting an unacceptable level of the bone cement during the mixing phase, a second threshold for detecting an unacceptable level of the bone cement during the application gun preparation phase, a third threshold for detecting an unacceptable level of the bone cement during the application gun use phase, and a fourth threshold for detecting an unacceptable level of the bone cement after mixing is complete and when the application gun is not being prepared or used. The system can e.g. access a threshold database/repository storing a respective threshold for each milestone specific to bone cement, including the first, second, third, and fourth thresholds. Based on the detected substance in block 202 (e.g., bone cement) and the determined surgical milestone in block 204, the system can retrieve the threshold associated with bone cement and the surgical milestone. The first threshold may be higher than the second and/or third threshold; the second and/or third threshold may be higher than the fourth threshold. This may be because a relatively high level of bone cement vapor may be expected in the environment during the mixing phase especially if an open mixing bowl is used or no vacuum/ventilation system is operating; accordingly, the first threshold may be relatively higher to prevent excessive triggering of the threshold. During the gun preparation phase and/or the gun use phase, a relatively moderate level of bone cement vapor may be expected as cement is inserted into the application gun and/or used during the procedure. After mixing, the mixing bowl may be moved to a back table and typically covered to prevent vapor from escaping into environment; thus, a relatively low level of bone cement vapor may be expected. Accordingly, the associated thresholds may be set accordingly.

The system can provide a user interface for specifying the type of substance for detection and/or the acceptable threshold or range for the substance. For example, an administration console can be provided for defining target gases for detection as well as unsafe thresholds per specified gas type.

At block 208, the system determines that the quantity of the substance detected in block 202 exceeds a threshold associated with the substance and the surgical milestone of the surgery in the operating room. At block 210, in accordance with the determination that the quantity of the substance exceeds the threshold associated with the substance and the surgical milestone, the system outputs a notification that the quantity of the substance exceeds the threshold associated with the substance and the surgical milestone. The notification can for example be displayed on a display in the operating room. As shown in the example in FIG. 1, the notification can be displayed on the display 112 in the operating room 100. Alternatively, or additionally, the system displays the notification on a display in a monitoring area. As shown in the example in FIG. 1, an output can be displayed on the display 126, which can be a monitor at a central control/command center for monitoring multiple operating rooms. Alternatively, or additionally, the system displays the notification as a message (e.g., a text message, a notification) on a mobile device. As shown in the example in FIG. 1, a notification can be displayed on the mobile phone 124. While the notifications shown in FIG. 1 are visual alerts, it should be appreciated that the notification can additionally or alternatively comprise an audio component, a haptic component, or any combination thereof. In some examples, the notification can be provided based on user-configurable settings (e.g., at a user-specified frequency). It should be understood that the aforementioned outputs are meant to be exemplary and not limiting. The system may be configured to provide a variety of different or additional outputs.

The alert can prompt a user to check an air management system associated with the operating room, check a WAG scavenging system associated with the operating room, check the WAGD system, check for a source of the substance (e.g., check the anesthesia machine to identify possible leaks), review a checklist, or any combination thereof. For example, the system can alert the maintenance department to check the function of WAG disposal system. If an institution has a WAGD system, the scavenging system may be connected directly to it through a dedicated WAGD vacuum port. As another example, the system may issue an alert for the OR anesthesia team to check the ventilations system and/or the scavenging system, check for spills or leakages, or to ensure that the patient's mask is fitting properly, that the intubation tubes or airway devices are inserted and functioning properly, etc. As another example, the system may issue an alert for the user to review a customized checklist (e.g., a checklist customized for WAG, a checklist customized for bone cement) selected based on the substance that triggered the threshold. As another example, the system may issue an alert to a remote anesthesia team or respiratory team that an unacceptable level of substance has been detected, allowing for additional experts to assist in troubleshooting the issue intraoperatively or postoperatively. As another example, the system may issue an alert to an institutional maintenance team of the issue, resulting in accelerated maintenance of possible contributing systems.

If the quantity of the substance exceeds the threshold associated with the substance and the surgical milestone, the system may additionally or alternatively transmit a control signal to an air management system to adjust the air management system. The air management system can comprise an air ventilation system, such as a positive pressure ventilation system for reducing risks of surgical site infection in the operating room. The control signal can cause an adjustment of the air exchange or turnover rate of the air ventilation system. An increased turnover rate can cause the air to be circulated or recycled at a higher rate to accelerate evacuation of WAG from the surgical environment. The system may additionally or alternatively re-route air flow to a different filtration system.

The turnover rate can be determined by the system based on the substance, a type of the surgery in the operating room, or any combination thereof. Certain types of target substances (e.g., certain types of gases) may expose the patient and the medical staff to higher risks than other types of target substances. Furthermore, for certain types of surgical procedure types (e.g., orthopedic and cardiac procedures), there is a greater concern for surgical site infections. Accordingly, depending on the substance that triggered the threshold and the type of surgery, the system can determine a higher turnover rate such that the air ventilation system can operate with the higher turnover rate to reduce the risk of infection/exposure.

If the quantity of the substance exceeds the threshold associated with the substance and the surgical milestone, the system may additionally or alternatively initiate automatic checks to ensure that the air management system is functioning properly. For example, the system can automatically obtain data on the air management system (e.g., the WAG scavenging system, or WAGD system) to ensure that it is not disabled or is functioning properly. As another example, the system can automatically obtain data on the anesthesia machine to determine whether it is functioning properly. If, for example, the anesthesia machine indicates that it is not currently outputting any anesthesia gas but the threshold for an unacceptable level of anesthesia gas has been triggered, the system may determine that the anesthesia machine may be leaking. The system can output the results of the automatic checks (e.g., on a dashboard in the OR).

If the quantity of the substance exceeds the threshold associated with the substance and the surgical milestone, the system may additionally or alternatively identify a source of the substance (e.g., a leak source) in the operating room. The system can make the identification using one or more machine-learning models, by receiving one or more images of the operating room captured by one or more cameras (e.g., cameras 102*a*, 102*b*, and 120) and identifying an event (e.g., improper fit of a patient's mask, spill of one or more liquid anesthesia agents) using one or more trained machine-learning models based on the received one or more images. The machine-learning models may be object detection/tracking models as described herein. In some examples, the system can make the identification using one or more multispectral or hyperspectral imaging sensors.

The system may store the detected quantity of the substance in a database (e.g., a database of the HIS or EMR system) for various downstream analyses. WAG measurements for a given surgical procedure may e.g. be recorded in a database periodically or when a threshold is triggered. Trend information may be analyzed to determine when maintenance on an anesthesia machine is required prematurely before any scheduled routine maintenance. For example, the system can determine if unscheduled or unplanned equipment maintenance is required by analyzing data in the database, such as maintenance on an air management system, a WAG scavenging system, WAGD system, and an anesthesia machine, etc. In some examples, the system can generate reports with historical data that can be reviewed by maintenance teams to predict issues and preemptively conduct preventive maintenance.

The system can be configured to determine an update to a surgical protocol by analyzing data in the database. For example, the system can identify correlations between exposure to a target substance and instances of illness in staff in the operating room (e.g., cancer). If a correlation is identified, the system may automatically formulate a protocol update, for example, to limit or control the amount of exposure to the substance during a surgery. The system can recommend, based on historical data and observation of trends, maintenance of equipment (e.g., anesthesia machines, scavenging system, WAG disposal systems, etc.) or facility systems (e.g., HVAC, laminar flow, etc.) through notifications to maintenance teams. For example, if the system determines that a device is not activated to emit a substance (e.g., based on the repository of device state data as described herein) but the substance is nevertheless detected in the environment, the system can recommend that the device be inspected and/or updated by the appropriate maintenance team. As another example, if an unacceptable level of the substance is detected, the system can recommend that the relevant equipment or facility systems be inspected and/or updated within a time frame. As another example, if the system detects an increase of the substance over time, the system can recommend that the relevant equipment or facility systems be inspected and/or updated before the level of the substance reaches an unacceptable level.

Figures 3A, 3B:
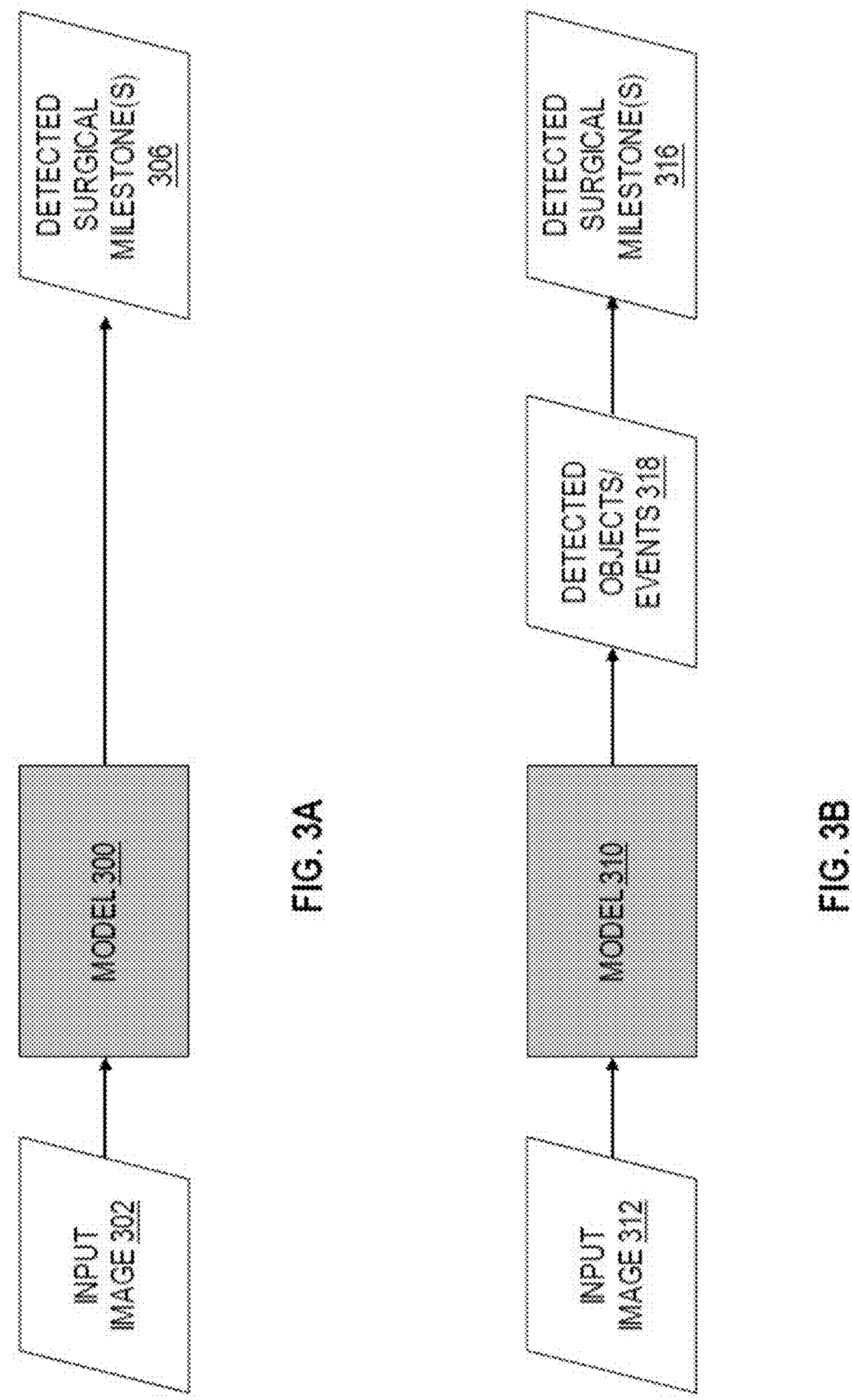
FIG. 3A illustrates an exemplary machine-learning model used to detect surgical milestones.
FIG. 3B illustrates an exemplary machine-learning model used to detect objects and/or events, which are in turn used to detect surgical milestones.

FIGS. 3A and 3B illustrate exemplary machine-learning models that can be used to detect surgical milestone(s), in accordance with some examples. Both models 300 and 310 can receive an input image. The model(s) 300 can be configured to directly output one or more surgical milestones depicted in the input image. In contrast, the model(s) 310 can be configured to output one or more detected objects or events 318, which in turn can be used by the system to determine one or more surgical milestones depicted in the input image. Models 300 and 310 are described in detail below.

With reference to FIG. 3A, a model 300 is configured to receive an input image 302 and directly output an output 306 indicative of one or more surgical milestones detected in the input image 302. The model 300 can be trained using a plurality of training images depicting the one or more surgical milestones. For example, the model 300 can be trained using a plurality of annotated training images. Each of the annotated images can depict a scene of an operating room and include one or more labels indicating surgical milestone(s) depicted in the scene. For example, at least some of the annotated images are captured in the same operating room (e.g., operating room 100) for which the model will be deployed. During training, the model receives each image of the annotated images and provides an output indicative of detected surgical milestone(s). The output is compared against the labels associated with the image. Based on the comparison, the model 300 can be updated (e.g., via a backpropagation process).

With reference to FIG. 3B, a model 310 is configured to receive an input image 312 and output one or more detected objects and/or events 318 depicted in the input image 312. Based on the one or more detected objects and/or events 318, the system can determine, as output 316, one or more surgical milestones detected in the input image 312. The one or more machine learning models can be trained using a plurality of training images depicting the one or more objects and/or events. For example, the model 310 can be trained using a plurality of annotated training images. Each of the annotated images can depict a scene of an operating room and include one or more labels indicating objects and/or events depicted in the scene. At least some of the annotated images can be captured in the same operating room (e.g., operating room 100) for which the model will be deployed. During training, the model receives each image of the annotated images and provides an output indicative of one or more detected objects and/or events. The output is compared against the labels associated with the image. Based on the comparison, the model 300 can be updated (e.g., via a backpropagation process).

The addition of other types of sensing technologies and intelligence to the OR can assist in realizing improved benefits for patients, health care professionals (HCP), and institutions.

For example, surgical site infections is a health risk for patients and a concern for hospitals as it could affect potential for reimbursements and therefore revenue. The risk of SSI may increase as a result of reduction in core body temperature during preoperative preparation while in the OR. Sensing technologies (e.g. thermal sensors embedded in surgical table pads, thermal camera in surgical light or elsewhere in the OR infrastructure) can be utilized to monitor patient temperature changes during the full spectrum of stay in the OR and alert HCPs if a threshold is exceeded such that appropriate action can be taken. Sensor measurements can be recorded in EMR for future data analysis and outcome correlations.

Further, examples of the present disclosure can be used for prevention and reduction of occurrence of pressure sores developed while the patient uses hospital beds. As much as 20% of pressure sore occur or begin during the surgical procedure. Sensing technologies (e.g. pressure sensors embedded in surgical table pads, video cameras in surgical light or elsewhere in OR infrastructure) can be utilized to monitor how long the patient remains without position adjustment during the full spectrum of stay in the OR and alert HCPs to take appropriate action to relieve pressure on high risk tissue areas to prevent development of pressure sores. Sensor measurements can be recorded in EMR for future data analysis and outcome correlations.

Figure 4:
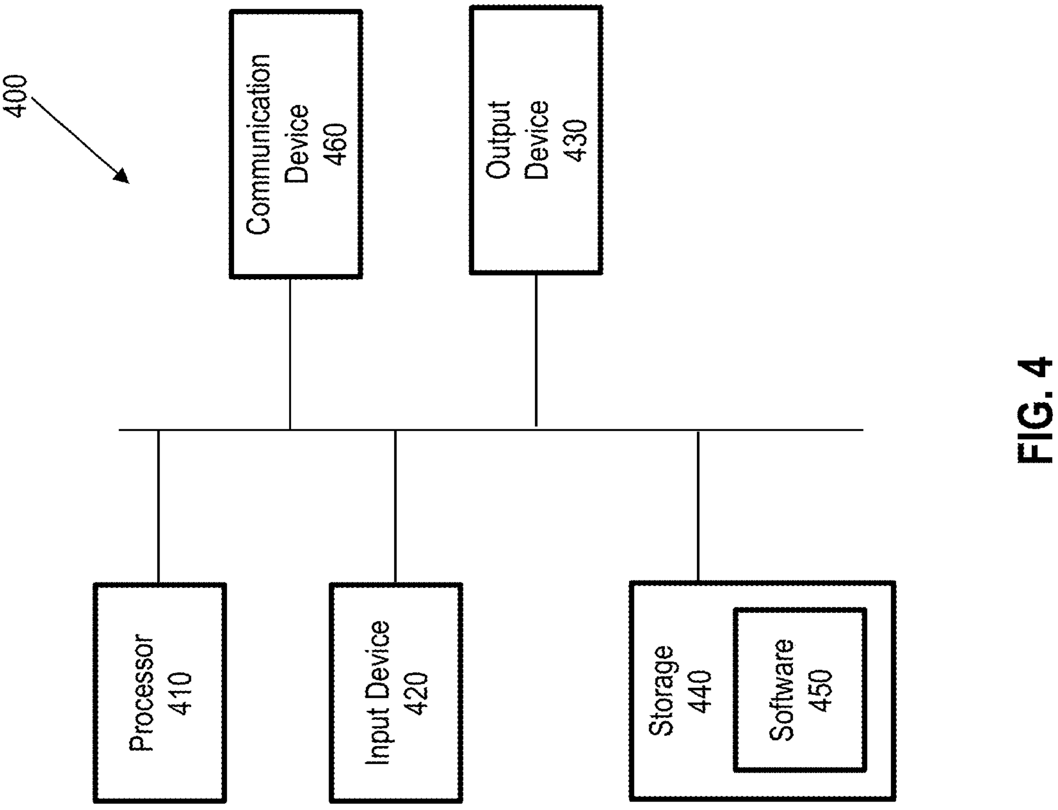
FIG. 4 depicts an exemplary electronic device.

The operations described herein are optionally implemented by components depicted in FIG. 4. FIG. 4 illustrates an example of a computing device. Device 400 can be a host computer connected to a network. Device 400 can be a client computer or a server. As shown in FIG. 4, device 400 can be any suitable type of microprocessor-based device, such as a personal computer, workstation, server or handheld computing device (portable electronic device) such as a phone or tablet. The device can include, for example, one or more of processor 410, input device 420, output device 430, storage 440, and communication device 460. Input device 420 and output device 430 can generally correspond to those described above, and can either be connectable or integrated with the computer.

Input device 420 can be any suitable device that provides input, such as a touch screen, keyboard or keypad, mouse, or voice-recognition device. Output device 430 can be any suitable device that provides output, such as a touch screen, haptics device, or speaker.

Storage 440 can be any suitable device that provides storage, such as an electrical, magnetic or optical memory including a RAM, cache, hard drive, or removable storage disk. Communication device 460 can include any suitable device capable of transmitting and receiving signals over a network, such as a network interface chip or device. The components of the computer can be connected in any suitable manner, such as via a physical bus or wirelessly.

Software 440, which can be stored in storage 440 and executed by processor 410, can include, for example, the programming that embodies the functionality of the present disclosure (e.g., as embodied in the devices as described above).

Software 440 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 440, that can contain or store programming for use by or in connection with an instruction execution system, apparatus, or device.

Software 440 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 400 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T4 lines, cable networks, DSL, or telephone lines.

Device 400 can implement any operating system suitable for operating on the network. Software 440 can be written in any suitable programming language, such as C, C++, Java or Python. In various examples, application software embodying the functionality of the present disclosure can be deployed in different configurations, such as in a client/server arrangement or through a Web browser as a Web-based application or Web service, for example.

The disclosure will now be further described by the following numbered embodiments which are to be read in connection with the preceding paragraphs, and which do not limit the disclosure. The features, options and preferences as described above apply also to the following embodiments.

Embodiment 1. A method for managing air quality associated with an operating room, comprising:

detecting a quantity of a substance in the air in the operating room;

determining a surgical milestone associated with a surgery in the operating room;

identifying a threshold associated with the substance and the surgical milestone of the surgery in the operating room;

determining that the quantity of the substance exceeds the threshold associated with the substance and the surgical milestone of the surgery in the operating room; and in accordance with the determination that the quantity of the substance exceeds the threshold associated with the substance and the surgical milestone, outputting a notification that the quantity of the substance exceeds the threshold associated with the substance and the surgical milestone.

Embodiment 2. The method of Embodiment 1, wherein the substance comprises an anesthesia gas.

Embodiment 3. The method of Embodiment 2, wherein the substance comprises nitrous oxide, desflurane, sevoflurane, enflurane, isoflurane, or any combination thereof.

Embodiment 4. The method of Embodiment 1, wherein the substance comprises bone cement.

Embodiment 5. The method of any of Embodiments 1-4, wherein the quantity of the substance in the air in the operating room is detected using one or more sensors in the operating room.

Embodiment 6. The method of any of Embodiments 1-5, wherein determining the surgical milestone associated with the surgery comprises:

receiving one or more images of the operating room captured by one or more cameras;

identifying the surgical milestone from a plurality of predefined surgical milestones using one or more trained machine-learning models based on the received one or more images.

Embodiment 7. The method of Embodiment 6, wherein the substance comprises an anesthesia gas, and wherein the plurality of predefined surgical milestones comprises: induction, intubation, anesthesia, extubation, or completion of the surgery.

Embodiment 8. The method of Embodiment 6, wherein the substance comprises bone cement, and wherein the plurality of predefined surgical milestones comprises: a mixing phase, a gun preparation phase, or a gun use phase.

Embodiment 9. The method of any of Embodiments 1-8, further comprising: transmitting a control signal to an air management system to adjust the air management system if the quantity of the substance exceeds the threshold associated with the substance and the surgical milestone.

Embodiment 10. The method of Embodiment 9, wherein the air management system comprises an air ventilation system, and wherein transmitting the control signal to the air management system to adjust the air management system comprises transmitting the control signal to the air ventilation system to adjust a turnover rate of the air ventilation system.

Embodiment 11. The method of Embodiment 10, further comprising: determining the turnover rate based on the substance, a type of the surgery in the operating room, or any combination thereof.

Embodiment 12. The method of any of Embodiments 1-11, further comprising re-routing air flow to a different filtration system if the quantity of the substance exceeds the threshold associated with the substance and the surgical milestone.

Embodiment 13. The method of any of Embodiments 1-12, further comprising identifying a source of the substance in the operating room if the quantity of the substance exceeds the threshold associated with the substance and the surgical milestone.

Embodiment 14. The method of Embodiment 13, wherein identifying the source of the substance in the operating room comprises:

receiving one or more images of the operating room captured by one or more cameras;

identifying an event using one or more trained machine-learning models based on the received one or more images.

Embodiment 15. The method of Embodiment 14, wherein the event is improper fit of a patient's mask, improper insertion of breathing tubes or airway devices, or any combination thereof.

Embodiment 16. The method of Embodiment 14, wherein the event is spill of one or more liquid anesthesia agents.

Embodiment 17. The method of Embodiment 14, wherein the source of the substance in the operating room is identified using one or more multispectral or hyperspectral imaging sensors.

Embodiment 18. The method of any of Embodiments 1-17, wherein the notification is an alert to:

check an air management system associated with the operating room;

check a waste anesthetic gas (WAG) scavenging system associated with the operating room;

check the waste anesthetic gas disposal (WAGD) system;

check for a source of the substance;

review a checklist; or any combination thereof.

Embodiment 19. The method of Embodiment 18, wherein the checklist is selected based on the substance.

Embodiment 20. The method of Embodiment 18, wherein the alert is visual, auditory, haptic, or any combination thereof.

Embodiment 21. The method of Embodiment 18, wherein the alert is displayed on a display in the operating room.

Embodiment 22. The method of any of Embodiments 1-21, further comprising: transmitting an alert to a remote anesthesia team or respiratory team if the quantity of the substance exceeds the threshold associated with the substance and the surgical milestone.

Embodiment 23. The method of any of Embodiments 1-22, further comprising: transmitting an alert to a maintenance team if the quantity of the substance exceeds the threshold associated with the substance and the surgical milestone.

Embodiment 24. The method of any of Embodiments 1-23, further comprising: providing a user interface for specifying the substance for detection.

Embodiment 25. The method of any of Embodiments 1-24, further comprising: providing a user interface for specifying the threshold.

Embodiment 26. The method of any of Embodiments 1-25, further comprising: storing the detected quantity of the substance in a database.

Embodiment 27. The method of Embodiment 26, further comprising: determining an update to a surgical protocol by analyzing data in the database.

Embodiment 28. The method of Embodiment 26, further comprising: determining if unscheduled or unplanned equipment maintenance is required by analyzing data in the database, wherein the equipment is any one of an air management system, a WAG scavenging system, WAGD system, and an anesthesia machine.

Embodiment 29. The method of any of Embodiments 1-28, wherein determining the surgical milestone associated with a surgery in the operating room comprises: receiving one or more images captured by a camera in the operating room; and providing the one or more images to a machine-learning model.

Embodiment 30. A system for managing air quality associated with an operating room, comprising:

one or more processors;

a memory; and one or more programs, wherein the one or more programs are stored in the memory and configured to be executed by the one or more processors, the one or more programs including instructions for:

detecting a quantity of a substance in the air in the operating room;

determining a surgical milestone associated with a surgery in the operating room;

identifying a threshold associated with the substance and the surgical milestone of the surgery in the operating room;

determining that the quantity of the substance exceeds the threshold associated with the substance and the surgical milestone of the surgery in the operating room; and in accordance with the determination that the quantity of the substance exceeds the threshold associated with the substance and the surgical milestone, outputting a notification that the quantity of the substance exceeds the threshold associated with the substance and the surgical milestone.

Embodiment 31. The system of Embodiment 30, wherein the substance comprises an anesthesia gas.

Embodiment 32. The system of Embodiment 31, wherein the substance comprises nitrous oxide, desflurane, sevoflurane, enflurane, isoflurane, or any combination thereof.

Embodiment 33. The system of Embodiment 30, wherein the substance comprises bone cement.

Embodiment 34. The system of any of Embodiments 30-33, wherein the quantity of the substance in the air in the operating room is detected using one or more sensors in the operating room.

Embodiment 35. The system of any of Embodiments 30-34, wherein determining the surgical milestone associated with the surgery comprises:

receiving one or more images of the operating room captured by one or more cameras;

identifying the surgical milestone from a plurality of predefined surgical milestones using one or more trained machine-learning models based on the received one or more images.

Embodiment 36. The system of Embodiment 35, wherein the substance comprises an anesthesia gas, and wherein the plurality of predefined surgical milestones comprises: induction, intubation, anesthesia, extubation, or completion of the surgery.

Embodiment 37. The system of Embodiment 35, wherein the substance comprises bone cement, and wherein the plurality of predefined surgical milestones comprises: a mixing phase, a gun preparation phase, or a gun use phase.

Embodiment 38. The system of any of Embodiments 30-37, wherein the one or more programs further include instructions for: transmitting a control signal to an air management system to adjust the air management system if the quantity of the substance exceeds the threshold associated with the substance and the surgical milestone.

Embodiment 39. The system of Embodiment 38, wherein the air management system comprises an air ventilation system, and wherein transmitting the control signal to the air management system to adjust the air management system comprises transmitting the control signal to the air ventilation system to adjust a turnover rate of the air ventilation system.

Embodiment 40. The system of Embodiment 39, wherein the one or more programs further include instructions for: determining the turnover rate based on the substance, a type of the surgery in the operating room, or any combination thereof.

Embodiment 41. The system of any of Embodiments 30-40, wherein the one or more programs further include instructions for re-routing air flow to a different filtration system if the quantity of the substance exceeds the threshold associated with the substance and the surgical milestone.

Embodiment 42. The system of any of Embodiments 30-41, wherein the one or more programs further include instructions for identifying a source of the substance in the operating room if the quantity of the substance exceeds the threshold associated with the substance and the surgical milestone.

Embodiment 43. The system of Embodiment 42, wherein identifying the source of the substance in the operating room comprises:

receiving one or more images of the operating room captured by one or more cameras;

identifying an event using one or more trained machine-learning models based on the received one or more images.

Embodiment 44. The system of Embodiment 43, wherein the event is improper fit of a patient's mask, improper insertion of breathing tubes or airway devices, or any combination thereof.

Embodiment 45. The system of Embodiment 43, wherein the event is spill of one or more liquid anesthesia agents.

Embodiment 46. The system of Embodiment 43, wherein the source of the substance in the operating room is identified using one or more multispectral or hyperspectral imaging sensors.

Embodiment 47. The system of any of Embodiments 30-46, wherein the notification is an alert to:

check an air management system associated with the operating room;

check a waste anesthetic gas (WAG) scavenging system associated with the operating room;

check the waste anesthetic gas disposal (WAGD) system;

check for a source of the substance;

review a checklist; or any combination thereof.

Embodiment 48. The system of Embodiment 47, wherein the checklist is selected based on the substance.

Embodiment 49. The system of Embodiment 47, wherein the alert is visual, auditory, haptic, or any combination thereof.

Embodiment 50. The system of Embodiment 47, wherein the alert is displayed on a display in the operating room.

Embodiment 51. The system of any of Embodiments 30-50, wherein the one or more programs further include instructions for: transmitting an alert to a remote anesthesia team or respiratory team if the quantity of the substance exceeds the threshold associated with the substance and the surgical milestone.

Embodiment 52. The system of any of Embodiments 30-51, wherein the one or more programs further include instructions for: transmitting an alert to a maintenance team if the quantity of the substance exceeds the threshold associated with the substance and the surgical milestone.

Embodiment 53. The system of any of Embodiments 30-52, wherein the one or more programs further include instructions for: providing a user interface for specifying the substance for detection.

Embodiment 54. The system of any of Embodiments 30-53, wherein the one or more programs further include instructions for: providing a user interface for specifying the threshold.

Embodiment 55. The system of any of Embodiments 30-54, wherein the one or more programs further include instructions for: storing the detected quantity of the substance in a database.

Embodiment 56. The system of Embodiment 55, wherein the one or more programs further include instructions for: determining an update to a surgical protocol by analyzing data in the database.

Embodiment 57. The system of Embodiment 55, wherein the one or more programs further include instructions for: determining if unscheduled or unplanned equipment maintenance is required by analyzing data in the database, wherein the equipment is any one of an air management system, a WAG scavenging system, WAGD system, and an anesthesia machine.

Embodiment 58. The system of any of Embodiments 30-57, wherein determining the surgical milestone associated with a surgery in the operating room comprises: receiving one or more images captured by a camera in the operating room; and providing the one or more images to a machine-learning model.

Embodiment 59. A non-transitory computer-readable storage medium storing one or more programs, the one or more programs comprising instructions, which when executed by one or more processors of an electronic device, cause the electronic device to perform any of the methods of Embodiments 1-29.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

What is claimed is:

1. A method for managing air quality associated with an operating room, comprising:

detecting an identity of a substance in the air in the operating room;

detecting a quantity of the identified substance in the air in the operating room;

determining a first surgical milestone associated with a surgical procedure in the operating room, wherein the surgical procedure further has a second surgical milestone occurring during the same surgical procedure at a different time than the first surgical milestone;

identifying a first threshold associated with an acceptable amount of the identified substance in the air during the first surgical milestone of the surgical procedure in the operating room, wherein identifying the first threshold associated with the acceptable amount of the identified substance in the air during the first surgical milestone of the surgical procedure in the operating room comprises selecting the first threshold from a plurality of thresholds, wherein the first threshold is different from a second threshold that is associated with an acceptable amount of the identified substance in the air during the second surgical milestone;

determining that the quantity of the identified substance exceeds the first threshold associated with the acceptable amount of the identified substance in the air during the first surgical milestone of the surgical procedure in the operating room; and in accordance with the determination that the quantity of the identified substance exceeds the first threshold associated with the acceptable amount of the identified substance in the air during the first surgical milestone, outputting a notification that the quantity of the identified substance exceeds the first threshold associated with the acceptable amount of the identified substance in the air during the first surgical milestone.

2. The method of claim 1, wherein the substance comprises an anesthesia gas or bone cement.

3. The method of claim 1, wherein the quantity of the identified substance in the air in the operating room is detected using one or more sensors in the operating room.

4. The method of claim 1, wherein determining the first surgical milestone associated with the surgical procedure comprises:

receiving one or more images of the operating room captured by one or more cameras; and identifying the first surgical milestone from a plurality of predefined surgical milestones using one or more trained machine-learning models based on the received one or more images.

5. The method of claim 4, wherein the substance comprises an anesthesia gas, and wherein the plurality of predefined surgical milestones comprises: induction, intubation, anesthesia, extubation, or completion of the surgery.

6. The method of claim 4, wherein the substance comprises bone cement, and wherein the plurality of predefined surgical milestones comprises: a mixing phase, a gun-preparation phase, or a gun-use phase.

7. The method of claim 1, further comprising: transmitting a control signal to an air management system to adjust the air management system if the quantity of the identified substance exceeds the first threshold associated with the acceptable amount of the identified substance in the air during the first surgical milestone.

8. The method of claim 7, wherein the air management system comprises an air ventilation system, and wherein transmitting the control signal to the air management system to adjust the air management system comprises transmitting the control signal to the air ventilation system to adjust a turnover rate of the air ventilation system.

9. The method of claim 1, further comprising re-routing air flow to a different filtration system if the quantity of the identified substance exceeds the first threshold associated with the acceptable amount of the identified substance in the air during the first surgical milestone.

10. The method of claim 1, further comprising identifying a source of the identified substance in the operating room if the quantity of the identified substance exceeds the first threshold associated with the acceptable amount of the identified substance in the air during the first surgical milestone.

11. The method of claim 10, wherein identifying the source of the identified substance in the operating room comprises:

receiving one or more images of the operating room captured by one or more cameras; and identifying an event using one or more trained machine-learning models based on the received one or more images.

12. The method of claim 11, wherein the event is improper fit of a patient's mask, improper insertion of breathing tubes or airway devices, spill of one or more liquid anesthesia agents, or any combination thereof.

13. The method of claim 10, wherein the source of the identified substance in the operating room is identified using one or more multispectral or hyperspectral imaging sensors.

14. The method of claim 1, wherein the notification is an alert to:

check an air management system associated with the operating room;

check a WAG scavenging system associated with the operating room;

check the WAGD system;

check for a source of the substance;

review a checklist selected based on the substance; or any combination thereof.

15. The method of claim 1, further comprising: transmitting an alert to a remote anesthesia team, a remote respiratory team, or a maintenance team if the quantity of the identified substance exceeds the first threshold associated with the acceptable amount of the identified substance in the air during the first surgical milestone.

16. The method of claim 1, further comprising: storing the detected quantity of the identified substance in a database.

17. The method of claim 16, further comprising: determining an update to a surgical protocol or if unscheduled or unplanned equipment maintenance is required by analyzing data in the database.

18. The method of claim 1, wherein determining the first surgical milestone associated with the surgical procedure in the operating room comprises: receiving one or more images captured by a camera in the operating room and providing the one or more images to a machine-learning model.

19. A system for managing air quality associated with an operating room, comprising:

one or more processors;

a memory; and one or more programs, wherein the one or more programs are stored in the memory and configured to be executed by the one or more processors, the one or more programs including instructions for:

detecting an identity of a substance in the air in the operating room;

detecting a quantity of the identified substance in the air in the operating room;

determining a first surgical milestone associated with a surgical procedure in the operating room, wherein the surgical procedure further has a second surgical milestone occurring during the same surgical procedure at a different time than the first surgical milestone;

identifying a first threshold associated with an acceptable amount of the identified substance in the air during the first surgical milestone of the surgical procedure in the operating room, wherein identifying the first threshold associated with the acceptable amount of the identified substance in the air during the first surgical milestone of the surgical procedure in the operating room comprises selecting the first threshold from a plurality of thresholds, wherein the first threshold is different from a second threshold that is associated with an acceptable amount of the identified substance in the air during the second surgical milestone;

determining that the quantity of the identified substance exceeds the first threshold associated with the acceptable amount of the identified substance in the air during the first surgical milestone of the surgical procedure in the operating room; and in accordance with the determination that the quantity of the identified substance exceeds the first threshold associated with the acceptable amount of the identified substance in the air during the first surgical milestone, outputting a notification that the quantity of the identified substance exceeds the first threshold associated with the acceptable amount of the identified substance in the air during the first surgical milestone.

20. A non-transitory computer-readable storage medium storing one or more programs for managing air quality associated with an operating room, the one or more programs comprising instructions, which, when executed by one or more processors of an electronic device, cause the electronic device to:

detect an identity of a substance in the air in the operating room;

detect a quantity of the identified substance in the air in the operating room;

determine a first surgical milestone associated with a surgical procedure in the operating room, wherein the surgical procedure further has a second surgical milestone occurring during the same surgical procedure at a different time than the first surgical milestone;

identify a first threshold associated with an acceptable amount of the identified substance in the air during the first surgical milestone of the surgical procedure in the operating room, wherein identifying the first threshold associated with the acceptable amount of the identified substance in the air during the first surgical milestone of the surgery in the operating room comprises selecting the first threshold from a plurality of thresholds, wherein the first threshold is different from a second threshold that is associated with an acceptable amount of the identified substance in the air during the second surgical milestone;

determine that the quantity of the identified substance exceeds the first threshold associated with the acceptable amount of the identified substance in the air during the first surgical milestone of the surgical procedure in the operating room; and in accordance with the determination that the quantity of the identified substance exceeds the first threshold associated with the acceptable amount of the identified substance in the air during the first surgical milestone, output a notification that the quantity of the identified substance exceeds the first threshold associated with the acceptable amount of the substance in the air during the first surgical milestone.

* * * * *